US012599588B2

(12) United States Patent
Murata et al.

(10) Patent No.: US 12,599,588 B2
(45) Date of Patent: Apr. 14, 2026

(54) INHIBITOR FOR V-ATPASE ACTIVITY, ANTIBACTERIAL AGENT, MEDICINE, ANTIBACTERIAL METHOD AND SCREENING METHOD

(71) Applicant: Japan Science and Technology Agency, Kawaguchi (JP)

(72) Inventors: Takeshi Murata, Chiba (JP); Kouki Shimizu, Chiba (JP); Fabiana Lica Yakushiji, Chiba (JP); Katsuhiko Moriyama, Chiba (JP)

(73) Assignee: Japan Science and Technology Agency, Kawaguchi (JP)

( * ) Notice: Subject to any disclaimer, the term of this patent is extended or adjusted under 35 U.S.C. 154(b) by 995 days.

(21) Appl. No.: 17/423,598

(22) PCT Filed: Jan. 15, 2020

(86) PCT No.: PCT/JP2020/001047
§ 371 (c)(1),
(2) Date: Jul. 16, 2021

(87) PCT Pub. No.: WO2020/149295
PCT Pub. Date: Jul. 23, 2020

(65) Prior Publication Data
US 2022/0105076 A1 Apr. 7, 2022

(30) Foreign Application Priority Data
Jan. 18, 2019 (JP) ................................ 2019-006819

(51) Int. Cl.

| | |
|---|---|
| ***A61K 31/4184*** | (2006.01) |
| ***A61K 31/167*** | (2006.01) |
| ***A61K 31/4245*** | (2006.01) |
| ***A61K 31/426*** | (2006.01) |
| ***A61K 31/515*** | (2006.01) |
| ***A61P 31/04*** | (2006.01) |
| ***A61P 43/00*** | (2006.01) |
| ***C12Q 1/18*** | (2006.01) |

(52) U.S. Cl.
CPC ...... *A61K 31/4184* (2013.01); *A61K 31/4245* (2013.01); *A61K 31/426* (2013.01); *A61K 31/515* (2013.01); *A61P 31/04* (2018.01); *C12Q 1/18* (2013.01)

(58) Field of Classification Search
CPC .. C07D 401/12; C07D 401/14; C07D 405/14; A61P 35/00; A61K 31/4439; A61K 31/444; A61K 31/497
See application file for complete search history.

(56) References Cited

U.S. PATENT DOCUMENTS

| | | | |
|---|---|---|---|
| 5,942,532 | A | 8/1999 | Ohemeng et al. |
| 2017/0210741 | A1 | 7/2017 | Augelli-Szafran et al. |

FOREIGN PATENT DOCUMENTS

| | | | |
|---|---|---|---|
| EP | 0619298 | A2 | 10/1994 |
| JP | H08502725 | A | 3/1996 |

(Continued)

OTHER PUBLICATIONS

PubChem, PubChem ID 26975, 4-pentylphenol, 2005 (Year: 2005).*

(Continued)

*Primary Examiner* — Bruck Kifle
*Assistant Examiner* — Kevin S Martin
(74) *Attorney, Agent, or Firm* — The Webb Law Firm

(57) ABSTRACT

An inhibitor for $Na^+$-translocating V-ATPase activity including a compound represented by (1)

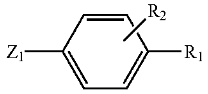

where $R_1$ represents a group selected from a hydroxy group, an alkoxy group, and a haloalkoxy group, each bonded to an adjacent phenyl group via oxygen, or a group selected from a dialkylamino group, a heterocyclic amine, and a carboxylic acid amide group, each bonded to an adjacent phenyl group via nitrogen, or represents bromine, iodine, or a straight-chain hydrocarbon group. $R_2$ represents hydrogen or a haloalkoxy group. $Z_1$ represents an aliphatic hydrocarbon group, an alicyclic hydrocarbon group, an aromatic hydrocarbon group, or a heterocyclic group, each optionally having an arbitrary substituent and having a structure containing a double bond selected from (1-1)

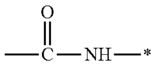

(1-2)

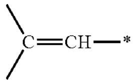

(1-3)

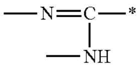

between the group and an adjacent phenyl group. The symbol * represents a bond to the adjacent phenyl group.

12 Claims, 8 Drawing Sheets

(56) References Cited

FOREIGN PATENT DOCUMENTS

| | | | |
|---|---|---|---|
| WO | 9404161 | A1 | 3/1994 |
| WO | 2014138833 | A1 | 9/2014 |

OTHER PUBLICATIONS

Sajjadifar et al. SBSA as a New and Efficient Catalyst for the One-Pot Green Synthesis of Benzimidazole Derivatives at Room Temperature, American Journal of Organic Chemistry, 2012, 2(2), pp. 1-6 (Year: 2012).*

Dictionary.com, in vitro, 2024 https://www.dictionary.com/browse/in-vitro (Year: 2024).*

Yalcin et al., QSARs of some novel antibacterial benzimidazoles, benzoxazoles, and oxazolopyridines against an enteric gram-negative rod; K. pneumoniae, International Journal of Pharmacuetics, 98, 1993, 1-8 (Year: 1993).*

Liss V et al. *Salmonella enterica* Remodels the Host Cell Endosomal System for Efficient Intravacuolar Nutrition. Cell Host Microbe. Mar. 8, 2017;21(3):390-402. doi: 10.1016/j.chom.2017.02.005. Epub Feb. 23, 2017. PMID: 28238623. (Year: 2017).*

Ravi O, Shaikh A, Upare A, Singarapu KK, Bathula SR. Benzimidazoles from Aryl Alkyl Ketones and 2-Amino Anilines by an Iodine Catalyzed Oxidative C(CO)-C(alkyl) Bond Cleavage. J Org Chem. Apr. 21, 2017;82(8):4422-4428. doi: 10.1021/acs.joc.7b00165. Epub Apr. 10, 2017. PMID: 28378580. (Year: 2017).*

Uzunoglu et al. 2-(p-Substituted phenyl)-5-substituted benzimidazole derivatives: synthesis and antiinflammatory and antimicrobial activities, Hacettepe Universitesi Eczacilik Fakultesi Dergisi (1997), Abstract (Year: 1997).*

Chaturvedi et al. A novel synthesis of 2-arylbenzimidazoles in molecular sieves-MeOH system and their antitubercular activity Bioorganic & Medicinal Chemistry 2018 4551-4559; SI Antitubercular assay. (Year: 2018).*

Biasotti et al., “Synthesis of Photoactivable Inhibitors of Osteoclast Vacuolar ATPase”, Bioorganic & Medical Chemistry, 2003, pp. 2247-2254, vol. 11.

Kakinuma, “Genetic Approach on Subunit Architecture of Sodium-translocating V-ATpase Complex”, Grant-in-Aid for Scientific Research Report, 5 pages, 2012, English-language Abstract.

Kobayashi, “Bacterial Adaptation to Change in Environmental pH”, Japanese Journal of Bacteriology, 1996, pp. 745-753, vol. 51:3, English-language Abstract.

Achance et al., “Deregulated Balance of Omega-6 and Omega-3 Polyunsaturated Fatty Acids following Infection by the Zoonotic Pathogen *Streptococcus suis*”, Infection and Immunity, May 2014, pp. 1778-1785, vol. 82:5.

Pauli et al., “Discovery of New Inhibitors of *Mycobacterium tuberculosis* InhA Enzyme Using Virtual Screening and a 3D-Pharmacophore-Based Approach”, Journal of Chemical Information and Modeling, Jul. 2013, pp. 2390-2401, vol. 53.

Yan Chengwen, “medical dialectics”, 1988, People’s Army Medical Publishing House.

* cited by examiner

INHIBITOR FOR V-ATPASE ACTIVITY, ANTIBACTERIAL AGENT, MEDICINE, ANTIBACTERIAL METHOD AND SCREENING METHOD

CROSS-REFERENCE TO RELATED APPLICATIONS

This application is the United States national phase of International Application No. PCT/JP2020/001047 filed Jan. 15, 2020, and claims priority to Japanese Patent Application No. 2019-006819 filed Jan. 18, 2019, the disclosures of which are hereby incorporated by reference in their entirety.

TECHNICAL FIELD

The present invention relates to an inhibitor for V-ATPase activity, an antibacterial agent, a medicine, an antibacterial method, and a screening method, and in particular, relates to an inhibitor for V-ATPase activity, which can efficiently inhibit V-ATPase existing in a microorganism that causes diseases and the like, an antibacterial agent, a medicine, an antibacterial method, and a screening method.

BACKGROUND ART

V-ATPase exists in an organelle membrane in eukaryotes, and is a supermolecular complex composed of a complicated subunit structure. The V-ATPase has a function as an ion-motive molecular motor, and transports ions between the inside and outside of the membrane while rotating a specific detail unit in the membrane by ATP hydrolysis energy. The V-ATPase is known to exist also in prokaryotes (bacteria), and may also be referred to as A-ATPase.

The V-ATPase is required to allow cells to grow in a specific environment. For example, in enterococci, the V-ATPase has a function to hydrolyze ATP and to transfer intracellular sodium ions ($Na^+$) to the outside of the cell, and by such a function, the enterococci can grow under high-salt concentration and high-pH conditions.

Further, the V-ATPase that is similar to that in enterococci exists in a variety of pathogenic microorganisms, and plays an important role in the growth under an alkaline condition. Accordingly, a compound that inhibits an ion transport function of V-ATPase is useful as an antibacterial agent for pathogens that cause diseases, and is expected as a new therapeutic agent.

Conventionally, as an antibacterial agent, various compounds are known. For example, U.S. Pat. No. 5,942,532 discloses that a 2-substituted benzimidazole having a specific structure is useful as an antibacterial agent.

CITATION LIST

Patent Literature

Patent Literature 1: U.S. Pat. No. 5,942,532 (for example, claim 1)

SUMMARY OF INVENTION

The antibacterial agent of U.S. Pat. No. 5,942,532 exerts an antibacterial action as a histidine protein kinase inhibitor for microorganisms, and is different from an antibacterial agent that inhibits V-ATPase.

An object of the present invention is to provide an inhibitor for V-ATPase activity, which can selectively and efficiently suppress the growth of the bacteria that cause diseases or the like, an antibacterial agent and a medicine, which contain the inhibitor for V-ATPase activity, and an antibacterial method. Further, another object of the present invention is to provide a screening method for efficiently screening such an inhibitor for V-ATPase activity.

The present inventors have conducted the intensive studies to solve the problem described above. As a result, the present inventors have found that a specific compound, which contains an aromatic ring, an electron-donating group bound to the aromatic ring, and an arbitrary substituent bound to the aromatic ring and having a double bond, exerts an effect of inhibiting the V-ATPase activity, and thus have completed the present invention.

That is, the present invention is an inhibitor for $Na^+$-translocating V-ATPase activity, which is characterized by including a compound represented by the following formula (1).

[Chemical formula 1]

(1)

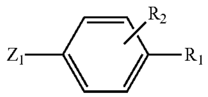

(In the formula, $R_1$ represents a group selected from a hydroxy group, an alkoxy group having 1 to 10 carbon atoms, and a haloalkoxy group having 1 to 3 carbon atoms, each bonded to an adjacent phenyl group via oxygen, or a group selected from a dialkylamino group having 1 to 10 carbon atoms of each alkyl group, a heterocyclic amine having 2 to 6 carbon atoms, and a carboxylic acid amide group optionally having a substituent bonded to a carbon atom, each bonded to an adjacent phenyl group via nitrogen, or represents bromine, iodine, or a straight-chain hydrocarbon group having 2 to 5 carbon atoms.

$R_2$ represents hydrogen or a haloalkoxy group having 1 to 3 carbon atoms.

$Z_1$ represents an aliphatic hydrocarbon group having 5 to 20 carbon atoms, an alicyclic hydrocarbon group having 3 to 20 carbon atoms, an aromatic hydrocarbon group having 6 to 20 carbon atoms, or a heterocyclic group having 2 to 20 carbon atoms, each optionally having an arbitrary substituent and having a structure containing a double bond selected from the following formulas (1-1) to (1-3) between the group and an adjacent phenyl group. The symbol * represents a bond to the adjacent phenyl group.)

[Chemical formula 2]

(1-1)

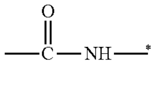

(1-2)

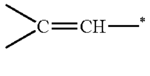

(1-3)

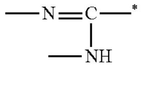

In this case, the compound represented by the formula (1) is preferably a 2-phenyl benzimidazole derivative represented by the following formula (2).

[Chemical formula 3]

(2)

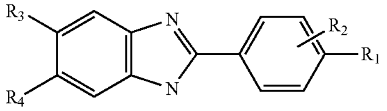

(In the formula, $R_1$ and $R_2$ are as defined in the formula (1), $R_3$ and $R_4$ represent a hydrogen atom, an alkyl group having 1 to 4 carbon atoms, or a halogen atom selected from fluorine, chlorine, bromine, and iodine, and $R_3$ and $R_4$ may be the same as or different from each other.)

Further, in the above case, the inhibitor for V-ATPase activity according to the present invention, which is characterized in that the compound represented by the above formula (1) is a (1,2,4-oxadiazol-3-yl)phenyl derivative represented by the following formula (7).

[Chemical formula 4]

(7)

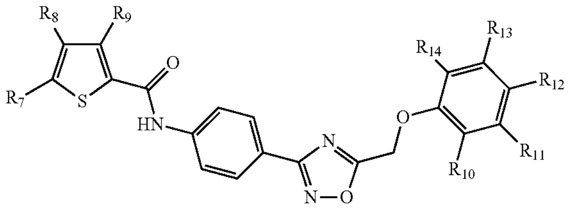

(In the formula, $R_7$ to $R_{14}$ each represent a hydrogen atom, an alkyl group having 1 to 4 carbon atoms, an amino group, an ether group, a sulfonyl group, a boron group, or a halogen atom selected from fluorine, chlorine, bromine, and iodine, and $R_7$ to $R_{14}$ may be the same as or different from one another.)

Furthermore, in the above case, the inhibitor is preferably characterized by binding to a membrane-embedded rotor ring (c ring) of V-ATPase and inhibiting the activity.

It is preferable that the compound represented by the above formula (1) is (Z)-5-(2,4-bis(difluoromethoxy)benzylidene)-2-(cyclopentyl amino)thiazol-4 (5H)-one, (2E,4E,6E,8E)-N-(4-hydroxyphenyl)-3,7-dimethyl-9-(2,6,6-trimethylcyclohexyl-1-en-1-yl)nona-2,4,6,8-tetraeneamide, 5-(4-(nonyloxy)benzylidene)pyrimidine-2,4,6(1H,3H,5H)-trione, N,N-dimethyl-4-(6-methyl-1H-benzo[d]imidazol-2-yl)aniline), or N-(4-(5-((o-tolyloxy)methyl)-1,2,4-oxadiazol-3-yl)phenyl)thiophene-2-carboxamide.

The present invention is an antibacterial agent against a bacterium having V-ATPase, which is characterized by including the inhibitor for V-ATPase activity described in any one of the above.

Moreover, the present invention is a medicine characterized by including the antibacterial agent described above.

The present invention is a bacterial flora control agent for selectively reducing a bacterium having V-ATPase from a bacterial flora containing the bacterium having V-ATPase and a bacterium having no V-ATPase, which is characterized by including the inhibitor for V-ATPase activity according to the present invention.

Further, the present invention is a medicine which is characterized by including the bacterial flora control agent described above.

Furthermore, the present invention is an antibacterial method for suppressing growth of a bacterium by using the antibacterial agent described above, which is characterized by including the steps of: administering the inhibitor for V-ATPase activity to a bacterium having V-ATPase; and binding the inhibitor for V-ATPase activity to a membrane-embedded rotor ring (c ring) of the V-ATPase of the bacterium and inhibiting the activity of the V-ATPase.

Moreover, the present invention is a screening method for selecting a candidate compound for an inhibitor for $Na^+$-translocating V-ATPase activity from test compounds, which is characterized by including the steps of: untreated evaluation of evaluating a living state of a bacterium having V-ATPase at a first pH and a second pH on the alkaline side of the first pH without bringing each of the test compounds into contact with the bacterium; treated evaluation of evaluating a living state of the bacterium at the first pH and the second pH after bringing each of the test compounds into contact with the bacterium; and candidate compound identification of identifying a test compound generating a difference in the living state between the steps of untreated evaluation and treated evaluation as a candidate compound for an antibacterial agent against the bacterium.

Further, the present invention is an antibacterial medicine including a compound having V-ATPase inhibitory activity as an active component.

Furthermore, the present invention is an antibacterial method, which is characterized by including the steps of: administering a compound having V-ATPase inhibitory activity to a bacterium having V-ATPase; and binding the inhibitor for V-ATPase activity to the V-ATPase of the bacterium and inhibiting the activity of the V-ATPase.

According to the present invention, an inhibitor for V-ATPase activity, which can selectively and efficiently suppress the growth of the bacteria that cause diseases or the like, an antibacterial agent and a medicine, which contain the inhibitor for V-ATPase activity, and an antibacterial method can be provided. Further, according to the present invention, a screening method for efficiently screening such an inhibitor for V-ATPase activity can be provided.

DESCRIPTION OF THE INVENTION

1. Inhibitor for V-ATPase Activity

Figure 1:
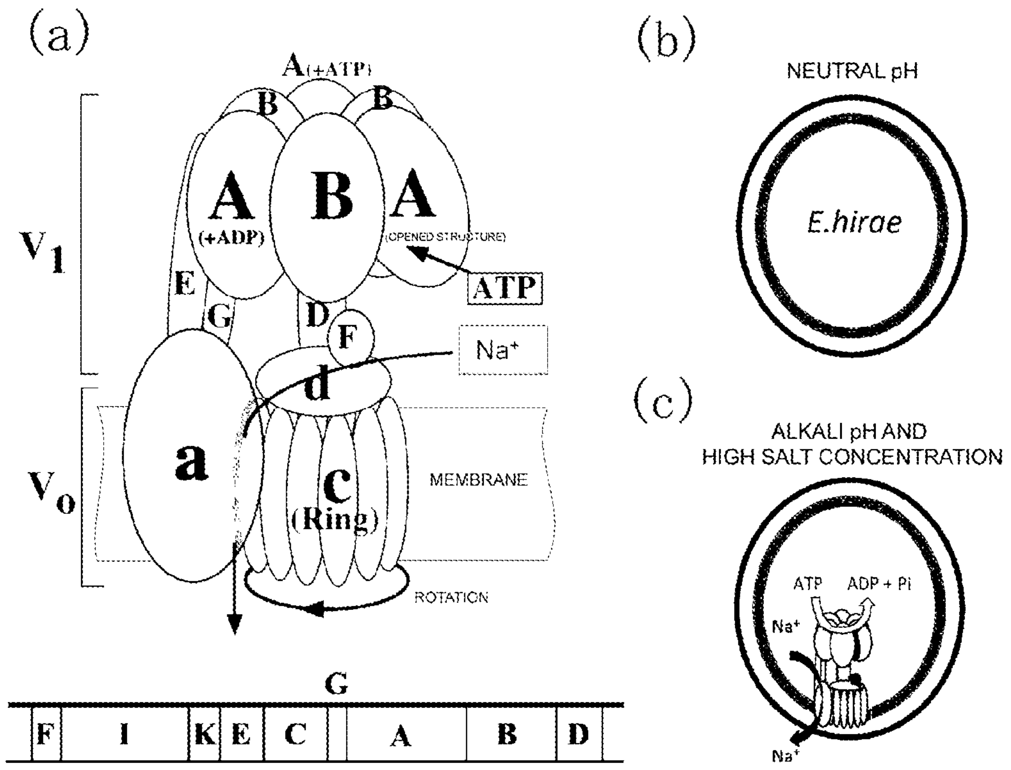
FIG. 1 is schematic diagrams showing the overall structure of V-ATPase and the expression under a specific environment.

The inhibitor for V-ATPase activity according to the present invention contains a compound that is an inhibitor for $Na^+$-translocating V-ATPase activity and is represented by the following formula (1).

[Chemical formula 5]

(1)

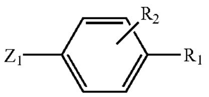

(In the formula, $R_1$ represents a group selected from a hydroxy group, an alkoxy group having 1 to 10 carbon atoms, and a haloalkoxy group having 1 to 3 carbon atoms, each bonded to an adjacent phenyl group via oxygen, or a group selected from a dialkylamino group having 1 to 10 carbon atoms of each alkyl group, a heterocyclic amine having 2 to 6 carbon atoms, and a carboxylic acid amide group optionally having a substituent bonded to a carbon atom, each bonded to an adjacent phenyl group via nitrogen, or represents bromine (Br), iodine (I), or a straight-chain hydrocarbon group having 2 to 5 carbon atoms.

$R_2$ represents hydrogen or a haloalkoxy group having 1 to 3 carbon atoms.

$Z_1$ represents an aliphatic hydrocarbon group having 5 to 20 carbon atoms, an alicyclic hydrocarbon group having 3 to 20 carbon atoms, an aromatic hydrocarbon group having 6 to 20 carbon atoms, or a heterocyclic group having 2 to 20 carbon atoms, each optionally having an arbitrary substituent and having a structure containing a double bond selected from the following formulas (1-1) to (1-3) between the group and an adjacent phenyl group. The symbol * represents a bond to the adjacent phenyl group.)

[Chemical formula 6]

(1-1)

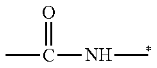

(1-2)

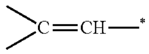

(1-3)

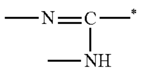

In $R_1$, the hydroxy group is a substituent represented by "—OH", and the alkoxy group having 1 to 10 carbon atoms is a substituent represented by "—O—$R_{1a}$" ($R_{1a}$ represents an alkyl group having 1 to 10 carbon atoms). Further, the haloalkoxy group having 1 to 3 carbon atoms in $R_1$ is a substituent represented by "—O—$R_{1b}$—$X_{n1}$" ($R_{1b}$ represents an alkyl group having 1 to 3 carbon atoms, X represents a halogen atom selected from fluorine, chlorine, bromine, and iodine, and n1=1 to 3). The dialkylamino group having 1 to 10 carbon atoms of each alkyl group is a substituent represented by "—N($R_{1c}$)($R_{1a}$)" ($R_{1c}$ represents an alkyl group having 1 to 10 carbon atoms, $R_{1d}$ represents an alkyl group having 1 to 10 carbon atoms, $R_{1c}$ and $R_{1d}$ may be the same as or different from each other). The heterocyclic amine having 2 to 6 carbon atoms is a substituent represented by "—N—$(CH_2)_{n2}$—" (n2=2 to 6). The carboxylic acid amide group is a substituent represented by "—NH—C(=O)—". The bromine is a substituent represented by "—Br", and the iodine is a substituent represented by "—I". The straight-chain hydrocarbon group having 2 to 5 carbon atoms is a substituent represented by "—$(CH_2)_{n3}$—$CH_3$" (n3=1 to 4).

In $R_2$, the hydrogen is a substituent represented by "—H". The haloalkoxy group having 1 to 3 carbon atoms is a substituent represented by "—O—$R_{2a}$—$X_{n4}$" ($R_{2a}$ represents a hydrocarbon group having 1 to 3 carbon atoms, X represents a halogen atom selected from fluorine, chlorine, bromine, and iodine, and n4=1 to 3). $R_2$ may be located at the ortho position or the meta position as viewed from $Z_1$ in the phenyl group.

In $Z_1$, the aliphatic hydrocarbon group having 5 to 20 carbon atoms is a substituent selected from an alkane, an alkene, an alkyne, an alkadiene, a conjugated diene, and the like.

Examples of the alkane having 5 to 20 carbon atoms include pentane, hexane, heptane, octane, nonane, decane, undecane, dodecane, tridecane, tetradecane, pentadecane, hexadecane, heptadecane, octadecane, nonadecane, and icosane.

Examples of the alkene having 5 to 20 carbon atoms include 1-pentene, 2-pentene, 1-hexene, 2-hexene, 3-hexene, 1-heptene, 2-heptene, 3-heptene, 4-heptene, 1-octene, 2-octene, 3-octene, 4-octene, 5-octene, 1-nonene, 2-nonene, 3-nonene, 4-nonene, 5-nonene, 1-decene, 2-decene, 3-decene, 4-decene, 5-decene, and 6-decene.

Examples of the alkyne having 5 to 20 carbon atoms include 1-pentyne, 2-pentyne, 1-hexyne, 2-hexyne, 3-hexyne, 1-heptyne, 2-heptyne, 3-heptyne, 4-heptyne, 1-octyne, 2-octyne, 3-octyne, 4-octyne, 5-octyne, 1-nonyne, 2-nonyne, 3-nonyne, 4-nonyne, 5-nonyne, 1-decene, 2-decene, 3-decene, 4-decene, 5-decene, and 6-decene.

Examples of the alkadiene having 5 to 20 carbon atoms include 1,3-pentadiene, 2,4-heptadiene, 1,4-pentadiene, 1,7-octadiene, 2,5-octadiene, and 2,6-octadiene.

Examples of the conjugated alkene having 5 to 20 carbon atoms include 1,3,5-heptatriene, 1,3,7-octatriene, 2,4,6-octatriene, 1,2,7,8-nonatetraene, 1,3,6,8-nonatetraene, 2,4,6,8-nonatetraene, 1,2,8,9-decatetraene, and 2,4,6,8-decatetraene.

The alicyclic hydrocarbon group having 3 to 20 carbon atoms is a substituent selected from a cycloalkane, a cycloalkene, a cycloalkyne, and the like. Examples of the alicyclic hydrocarbon group having 3 to 20 carbon atoms include cyclopropane, cyclobutane, cyclopentane, cyclohexane, cycloheptane, cyclooctane, cyclopropene, cyclobutene, cyclopropene, cyclohexene, cycloheptene, cyclooctene, and cyclooctyne.

Examples of the aromatic hydrocarbon group having 6 to 20 carbon atoms include benzene, naphthalene, and anthracene.

The heterocyclic group having 2 to 20 carbon atoms is a substituent having 2 to 20 carbon atoms and containing one or more elements selected from nitrogen, oxygen, and sulfur in the ring structure. Examples of the heterocyclic group having 2 to 20 carbon atoms include aziridine, oxirane, thiirane, 1H-azirine, 2H-azirine, oxirene, thiirene, azetidine, oxetane, thietane, azete, azolidine, oxolane, thiolane, azole, oxole, thiol, azinane, oxane, thiane, pyridine, azepane, oxepane, thiepane, azepine, oxepin, thiepin, imidazole, pyrazole, oxazole, thiazole, imidazoline, dioxane, morpholine, thiazine, triazole, tetrazole, dioxolane, pyridazine, pyrimidine, pyrazine, indole, isoindole, benzimidazole, purine, benzotriazole, quinoline, isoquinoline, quinazoline, quinoxaline, cinnoline, pteridine, chromene, isochromene, anthracene, acridine, xanthene, carbazole, oxadiazol, benzo-C-cinnoline (en), and tetracene.

In addition to the substituents described above, $Z_1$ may be a group in which to these substituents, 1 or 2 or more of an alkyl group, an alkenyl group, an alkynyl group, an aryl group, an oxo group, a halogen atom, a hydroxy group, a nitro group, a sulfo group, an ether group, a thiol group, an ester group, a carbonate group, carbonyl group, an amide group, an amino group, an azido group, a carbamate group, a cyano group, a hydroxy group, a carboxyl group, a sulfonic acid ester group, a sultone group, a lactone ring, a lactam ring, and the like are bound.

It is preferable that $Z_1$ contains a ring structure in the molecule. As the ring structure, a group selected from the above-described alicyclic hydrocarbon group having 3 to 20 carbon atoms, aromatic hydrocarbon group having 6 to 20 carbon atoms, and heterocyclic group having 2 to 20 carbon atoms is preferable. In $Z_1$, only one ring structure, or two or more ring structures may be contained. It is more preferable that the ring structure contains a structure containing a double bond represented by any one of the above formulas (1-1) to (1-3) in the molecule.

In particular, as the compound represented by the above formula (1), a 2-phenyl benzimidazole derivative represented by the following formula (2) is preferable.

[Chemical formula 7]

(2)

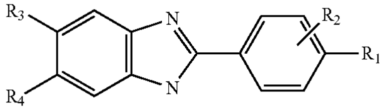

(In the formula, $R_1$ and $R_2$ are as defined in the formula (1), $R_3$ and $R_4$ represent a hydrogen atom, an alkyl group having 1 to 4 carbon atoms, or a halogen atom selected from fluorine, chlorine, bromine, and iodine, and $R_3$ and $R_4$ may be the same as or different from each other.)

As the 2-phenyl benzimidazole derivative represented by the above formula (2), compounds represented by the following formulas (V-161, V-161-01 to V-161-04, and V-161-10) can be included.

[Chemical formula 8]

(V-161)

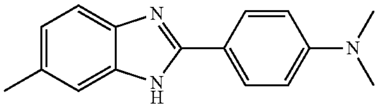

(V-161-01)

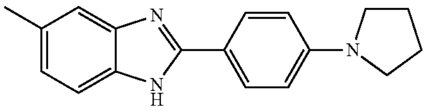

-continued (V-161-02)

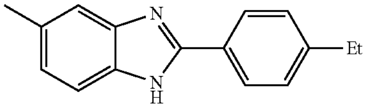

(V-161-03)

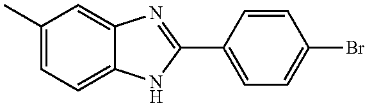

(V-161-04)

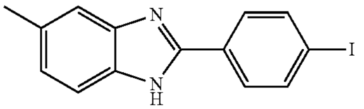

(V-161-10)

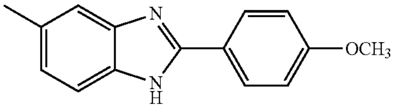

Among them, (N,N-dimethyl-4-(6-methyl-1H-benzo[d]imidazol-2-yl)aniline) represented by the formula V-161 is preferable since the effect of V-ATPase activity inhibition is high.

As the compound represented by the above formula (1), a (1,2,4-oxadiazol-3-yl)phenyl derivative represented by the following formula (6) can be included.

[Chemical formula 9]

(6)

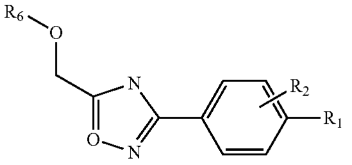

(In the formula, $R_1$ and $R_2$ are as defined in the formula (1). $R_6$ represents an aromatic hydrocarbon group having 6 to 20 carbon atoms, the aromatic hydrocarbon group may be replaced with an alkyl group having 1 to 4 carbon atoms.)

In particular, the compound represented by the formula (6) is preferably a (1,2,4-oxadiazol-3-yl)phenyl derivative represented by the following formula (7).

[Chemical formula 10]

(7)

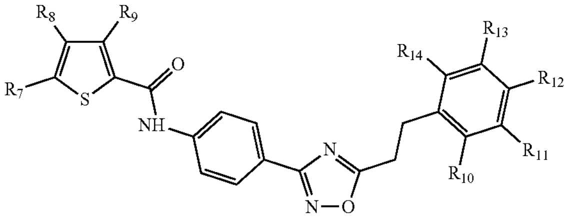

(In the formula, $R_7$ to $R_{14}$ each represent a hydrogen atom, an alkyl group having 1 to 4 carbon atoms, an amino group, an ether group, a sulfonyl group, a boron group, or a halogen atom selected from fluorine, chlorine, bromine, and iodine, and $R_7$ to $R_{14}$ may be the same as or different from one another.)

Specific examples of the compound represented by the following formula (7) include compounds represented by the following formulas (V-234), and (V-234-01) to (V-234-03).

V-234

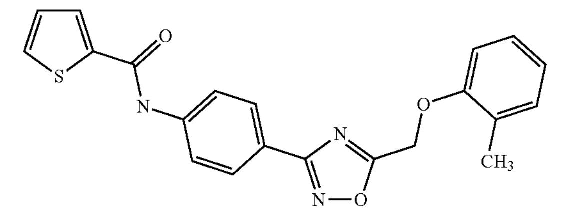

V-234-01

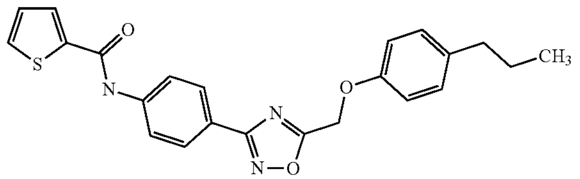

V-234-02

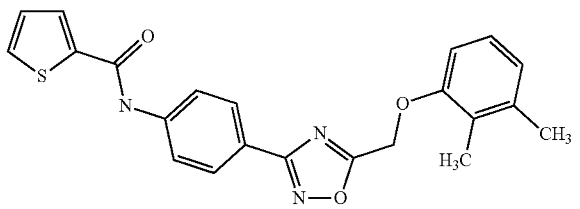

V-234-03

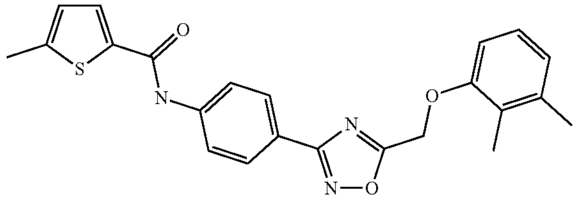

As the compound represented by the above formula (1), a compound represented by the following formula (3) can be included.

[Chemical formula 12]

(3)

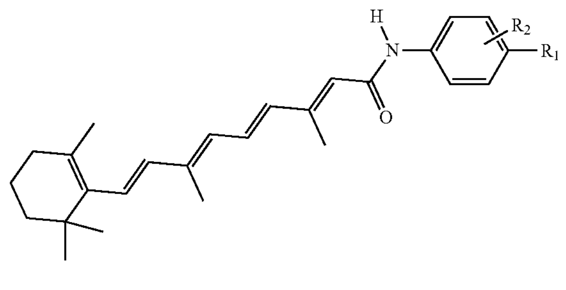

(In the formula, R1 and R2 are as defined in the formula (1).)

Further, as the compound represented by the above formula (1), a compound represented by the following formula (4) can be included.

[Chemical formula 13]

(4)

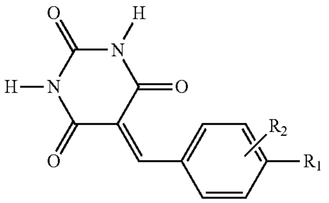

(In the formula, $R_1$ and $R_2$ are as defined in the formula (1).)

In addition, as the compound represented by the above formula (1), a compound represented by the following formula (5) can be included.

[Chemical formula 14]

(5)

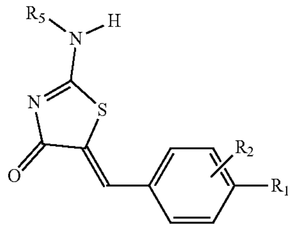

(In the formula, $R_1$ and $R_2$ are as defined in the formula (1). $R_5$ represents an alicyclic hydrocarbon group having 3 to 20 carbon atoms.)

As the compound represented by above formula (1), compounds shown below can be included.

[Chemical formula 15]

(V-6)

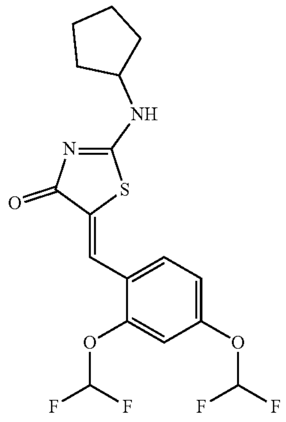

-continued (V-84)

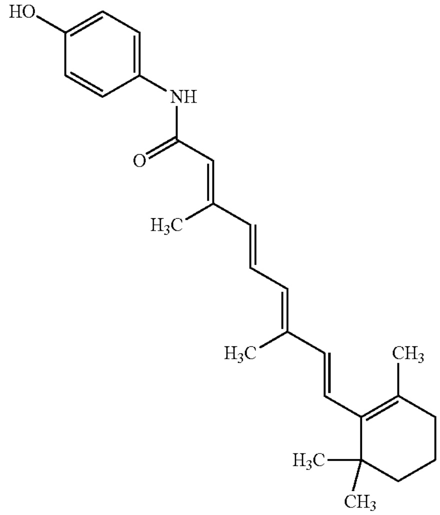

(V-130)

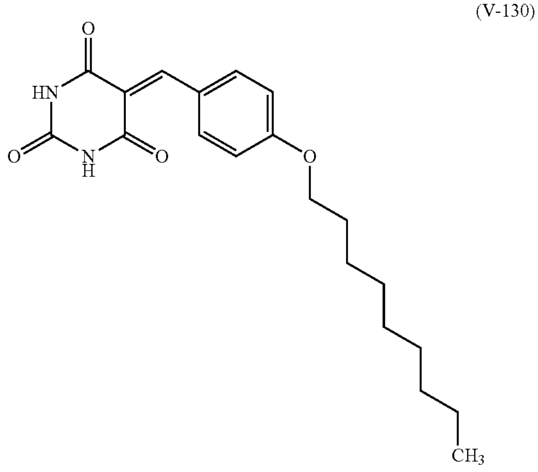

(V-161)

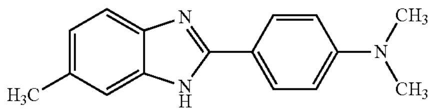

(V-234)

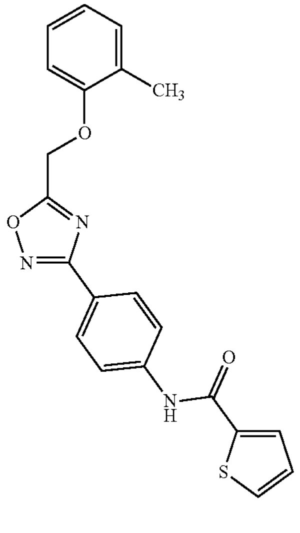

Names of these compounds are as follows.

V-6: (Z)-5-(2,4-bis(difluoromethoxy)benzylidene)-2-(cyclopentyl amino) thiazol-4 (5H)-one V-84: (2E,4E,6E,8E)-N-(4-hydroxyphenyl)-3,7-dimethyl-9-(2,6,6-trimethylcyclohexyl-1-en-1-yl)nona-2,4,6,8-tetraeneamide V-130: 5-(4-(nonyloxy)benzylidene)pyrimidine-2,4,6 (1H,3H,5H)-trione V-161: N,N-dimethyl-4-(6-methyl-1H-benzo[d]imidazol-2-yl)aniline)

V-234: N-(4-(5-((o-tolyloxy)methyl)-1,2,4-oxadiazol-3-yl)phenyl)thiophene-2-carboxamide Among them, compounds represented by V-6, V-161, and V-234 are particularly preferable, from the viewpoint that there are few non-specific bonds except to the V-ATPase.

2. V-ATPase Activity Inhibition Mechanism

Next, V-ATPase will be described. FIG. 1 is schematic diagrams of the V-ATPase of *Enterococcus hirae* (*E. hirae*) that is *Streptococcus* in the intestine, and shows $Na^+$-translocating V-ATPase. As shown in (a) of this figure, the V-ATPase is a complex composed of multiple subunits, and has a hydrophilic catalytic head portion ($V_1$ moiety) and an integral-membrane portion ($V_o$ moiety) responsible for the transportation of sodium ions ($Na^+$). The $V_1$ moiety is an ATP-driven motor portion, and the ATP is hydrolyzed by a $A_3B_3$ subunit to rotate the $V_1$ moiety. The $V_o$ moiety transports ions by using the rotational motion, and contains a membrane-embedded rotor ring (c ring) composed of a decamer of c subunit. The c ring has an ion-binding site, and is involved in the transport of ions between the inside and outside of the membrane. The V-ATPase hydrolyzes ATP by the $V_1$ moiety, and by using the energy from the hydrolysis, the c ring of the $V_o$ moiety is rotated to discharge sodium ions in the membrane to the outside.

In FIG. 1, (b) and (c) are schematic diagrams showing changes in the activity of V-ATPase in *E. hirae*, by the pH of the external environment. As shown in (b) of this figure, in the vicinity of a neutral pH (pH≤7.0), the V-ATPase is not expressed. On the other hand, as shown in (c) of this figure, under the pH (pH>7.0) on the alkaline side or the high salt concentration, V-ATPase is expressed, and sodium ions in the membrane are discharged to the outside. As a result, *E. hirae* keeps $Na^+$ low in cells and can grow even under the environment of alkali or the high salt concentration.

The inhibitor for V-ATPase activity according to the present invention has an action of binding to V-ATPase and inhibiting the activity. In particular, the inhibitor for V-ATPase activity according to the present invention has a function of binding to the c ring of V-ATPase and inhibiting the rotation, and thus inhibiting the transport of ions. Hereinafter, mechanism of the activity inhibition by the inhibitor for V-ATPase activity will be described.

The inhibitor for V-ATPase activity according to the present invention is a compound represented by the formula (1). As shown in the following formula, the compound has a phenyl group and an arbitrary substituent, and the phenyl group has a structure having an electron-donating group at the para position with respect to the binding position with the arbitrary substituent.

[Chemical formula 16]

(1)

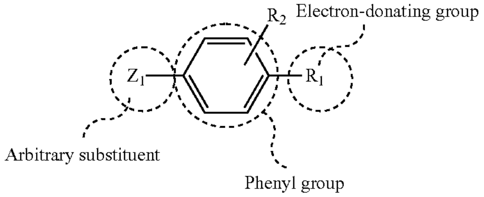

Further, diagrams for illustrating the structure of the inhibitor for V-ATPase activity mentioned above are shown. As shown in these diagrams, the arbitrary substituent Z1 is linked to the phenyl group via a structure containing a double bond represented by any one of the formulas (1-1) to (1-3). In addition, all of Z1 have a ring structure.

[Chemical formula 17]

(V-6)

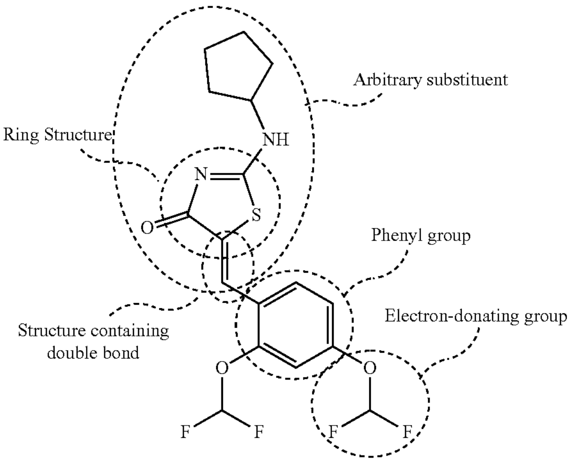

(V-84)

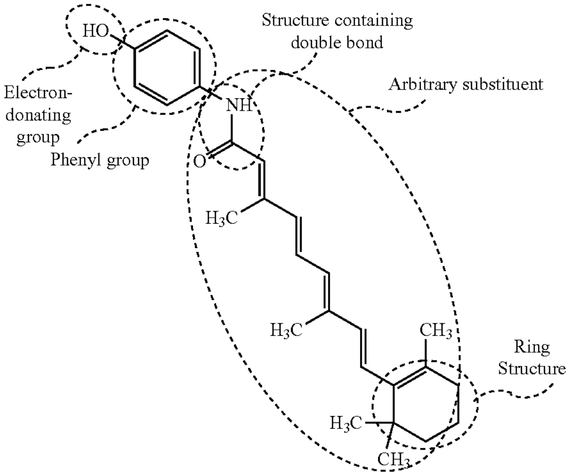

-continued (V-130)

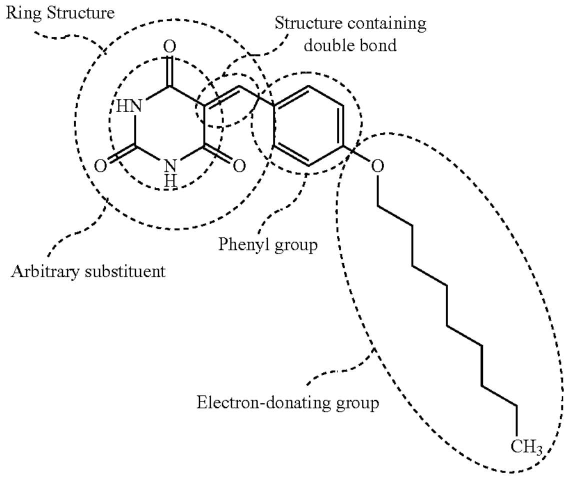

(V-161)

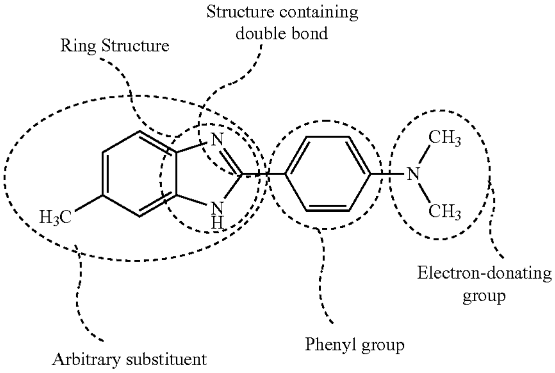

(V-234)

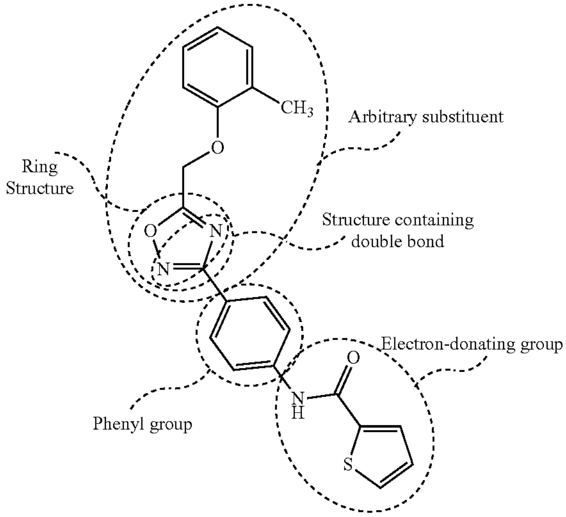

The phenyl group having an electron-donating group binds together with the arbitrary substituent to a specific site in the outer peripheral part of the c ring of V-ATPase, and is sandwiched between the c ring and the "a" subunit, and as a result of which the phenyl group plays a role of inhibiting the rotation of the c ring. The phenyl group and the arbitrary substituent are hydrophobic, and bind to the c ring by a hydrophobic interaction with an amino acid residue having a hydrophobic side chain in the outer peripheral part of the c ring. Further, it is considered that the electron density of π electrons of the benzene ring is increased by the electron-donating group bound to the para position of the phenyl group, and as a result of which the benzene ring is activated, and contributes to the binding affinity for the c ring of the inhibitor for V-ATPase activity. For example, in the compound "V-161" to be described later in Examples, interaction with an amino acid residue around a portion containing the 52nd phenylalanine of the c ring is performed, and the binding ability of the inhibitor is secured.

It is presumed that a hydrogen atom supplied from an NH group or the like of an arbitrary substituent and/or an electron-donating group serves as a donor, N, O, and S atoms serve as acceptors, and multiple hydrogen bonds are formed between the acceptors and the donors of the c ring. In this way, the arbitrary substituent and the electron-donating group contribute to the improvement of the binding affinity of V-ATPase with the c ring. The arbitrary substituent may have relatively any structure as long as it has an adequately large molecular weight and is hydrophobic. As the substituent, a substituent having a ring structure is preferable. By having a hydrophobic ring structure and increasing the bulkiness of the arbitrary substituent, the effect of inhibiting the rotation of the c ring by the inhibitor for V-ATPase activity is enhanced.

First, as the minimum basic structure required to bind to the c ring of V-ATPase, a structure containing a phenyl group and a double bond existing in a specific direction from the phenyl group is acceptable. In particular, in a case where the double bond represented by the formula (1-2) or (1-3) is adjacent to the phenyl group, it is considered that the structure is fixed by the resonance of the double bond and the phenyl group, and the resonated π-electrons play an important role in the binding to the c ring of V-ATPase.

In this regard, the structure containing a double bond may be contained in a linker linking a phenyl group and a ring structure (for example, V-84 or the like) in the arbitrary substituent, and may be contained in the ring structure in a case where there is no linker between the phenyl group and the ring structure (for example, V-161). Because of such a structure, the inhibitor for V-ATPase activity exerts an effect of inhibiting the V-ATPase activity by binding to the c ring of V-ATPase and suppressing the rotation.

3. Antibacterial Agent, Antibacterial Method, and Medicine

The inhibitor for V-ATPase activity according to the present invention inhibits the activity of V-ATPase as described above, and therefore, is useful as an antibacterial agent for microorganisms that express V-ATPase. A list of the microorganisms that express V-ATPase is shown in the following table. It is expected that the activity of V-ATPase of these microorganisms is inhibited by the inhibitor for V-ATPase activity according to the present invention and the growth of these microorganisms is suppressed. Further, the column of "Name of related disease" shows diseases that are expected to be treated or prevented by the growth suppression of microorganisms.

TABLE 1

| Bacteria | Name of related disease | V-ATPase ring identity (%) |
|---|---|---|
| *Chlamydia trachomatis* | Lymphogranuloma venereum, Trachoma | 99 |

TABLE 1-continued

| Bacteria | Name of related disease | V-ATPase ring identity (%) |
|---|---|---|
| *Mycobacterium abscessus* | Tuberculosis, Hansen's disease | 88 |
| *Enterococcus faecium* | Neonatal meningitis, Endocarditis | 99 |
| *Enterococcus durans* | Resistant bacterial infection | 98 |
| *Enterococcus mundtii* | Endophthalmitis | 97 |
| *Enterococcus faecalis* | Endocarditis, Sepsis, Meningitis | 96 |
| *Enterococcus malodoratus* | Endocarditis, Nosocomial infection, Urinary tract infection | 88 |
| *Enterococcus cecorum* | Poultry infection | 73 |
| *Enterococcus casseliflavus* | Bacteremia | 66 |
| *Streptococcus agalactiae* | Postpartum infection, Neonatal sepsis | 88 |
| *Streptococcus sanguinis* | Dental caries | 62 |
| *Streptococcus constellatus* | Pyogenic infection, Lung abscess, Cystic fibrosis | 61 |
| *Streptococcus intermedius* | Brain abscess, Liver abscess, Pyogenic abscess | 61 |
| *Streptococcus gallolyticus* | Endocarditis, Bacteremia, Colorectal cancer | 60 |
| *Streptococcus parasanguinis* | Endocarditis | 60 |
| *Streptococcus anginosus* | Brain tumor, Liver abscess, Bacteremia | 59 |
| *Streptococcus pyogenes* | Pharyngitis, Tonsillitis, Scarlet fever, Cellulitis, Erysipelas, Rheumatic Fever, Glomerulonephritis, Necrotizing fasciitis | 57 |
| *Streptococcus pneumoniae* | Pneumonia, Asthma, Rhinitis, Sinusitis, Conjunctivitis, Meningitis, Sepsis, Osteomyelitis, Endocarditis, Peritonitis, Pericarditis, Cellulitis, Brain abscess | 55 |
| *Streptococcus pseudopneumoniae* | Pneumonia | 55 |
| *Streptococcus mitis* | Endocarditis | 55 |
| *Streptococcus canis* | Poultry infection | 54 |
| *Streptococcus urinalis* | Urinary tract infection | 54 |
| *Clostridium botulinum* | Botulism | 65 |
| *Clostridium baratii* | Children botulism | 68 |
| *Clostridium argentinense* | Botulism | 61 |
| *Clostridium chauvoei* | Blackleg | 68 |
| *Clostridium intestinale* | Bacteremia | 57 |
| *Clostridium paraputrificum* | Bacteremia | 63 |
| *Clostridium perfringens* | Enterotoxemia, Gas gangrene, Food poisoning, Necrotic enteritis | 67 |
| *Clostridium tetani* | Tetanus | 58 |
| *Clostridium difficile* | Pseudomembranous colitis, Inflammatory diarrhea | 55 |
| *Fusobacterium nucleatum* | Periodontal disease, Colon cancer, Skin ulcer, Oral abscess, Pyomyositis, Pyogenic arthritis, Sepsis, Liver abscess, Intrauterine infection, Urinary tract infection, Endocarditis, Pneumonia | 61 |
| *Fusobacterium necrophorum* | Meningitis, Thrombosis | 57 |
| *Fusobacterium periodonticum* | Pseudomembranous colitis | 54 |
| *Abiotrophia defectiva* | Endocarditis | 59 |
| *Aerococcus urinae* | Urinary tract infection, Endocarditis, Sepsis, Cellulitis | 59 |
| *Aerococcus viridans* | Bacteremia | 61 |
| *Facklamia hominis* | Endocarditis | 63 |
| *Facklamia languida* | Infection | 66 |
| *Facklamia ignava* | Infection | 54 |
| *Facklamia sourekii* | Infection | 52 |
| *Alloiococcus otitis* | Otitis | 49 |

TABLE 1-continued

| Bacteria | Name of related disease | V-ATPase ring identity (%) |
|---|---|---|
| *Dolosigranulum pigrum* | Nosocomial pneumonia, Sepsis | 50 |
| *Granulicatella elegans* | Endocarditis | 68 |
| *Anaerotruncus colihominis* | Nosocomial sepsis | 54 |

In the table, the column of "Bacteria" shows name of microorganism, and the column of "Name of related disease" shows an example of the disease related to the microorganism. In addition, the column of "V-ATPase ring identity (%)" in the table shows the percent of homology between the c ring of V-ATPase of the microorganism and the c ring of *Enterococcus* V-ATPase. Regarding the *Enterococcus* V-ATPase, the present inventors have confirmed in Examples to be described later that the inhibitor for V-ATPase activity binds to the c ring of V-ATPase and exerts a growth suppressive effect of the *Enterococcus*. For this reason, a growth suppressive effect is expected to be exerted on a microorganism having V-ATPase that has a high homology with the c ring of *Enterococcus* V-ATPase by the inhibitor for V-ATPase activity according to the present invention in a similar manner as in the case of the *Enterococcus*. In addition, as described above, the inhibitor for V-ATPase activity interacts with the outer peripheral surface of the c ring, and the present inventors have confirmed that the amino acid sequence on the outer peripheral surface of the c ring of V-ATPase is relatively highly preserved in many microorganisms. For this reason, it is considered that even in a microorganism having a low homology with the c ring of *Enterococcus* V-ATPase, the inhibitor for V-ATPase activity is not always ineffective, and the growth suppressive effect of the microorganism may be exerted by the inhibitor for V-ATPase activity.

The inhibitor for V-ATPase activity according to the present invention is a novel antibacterial agent, and therefore, is expected to exert the effect even against drug-resistant bacteria that are resistant to conventional antibacterial agents. For example, the inhibitor for V-ATPase activity is useful also for *E. faecalis, E. faecium*, and the like, which are resistant to a drug such as vancomycin (vancomycin-resistant enterococci (VRE)).

The inhibitor for V-ATPase activity according to the present invention is useful as a bacterial flora control agent for selectively reducing a bacterium having V-ATPase from a bacterial flora containing the bacterium having V-ATPase and a bacterium having no V-ATPase.

For example, *Clostridium perfringens* or the like is a so-called bad bacterium, and is a pathogenic bacterium that decomposes proteins and produces harmful amines and carcinogenic substances in the intestine. Many of these microorganisms, which lead to deterioration of the intestinal environment, have V-ATPase and grow dominantly under an alkaline environment. On the other hand, bifidobacteria (belonging to the genus *Bifidobacterium*), lactic acid bacteria (belonging to the genus *Lactobacillus*), and the like are so-called good bacteria, ferment dietary fiber in the intestine and produce short-chain fatty acid that is important for maintaining the health of the host, such as butyric acid, or acetic acid, and suppress the growth of bad bacteria and the related diseases. Many of these microorganisms, which are helpful in improving the intestinal environment, have no V-ATPase. For this reason, the inhibitor for V-ATPase activity according to the present invention exerts an effect only on bad bacteria without exerting on the good bacteria, and selectively inhibits the growth of only the bad bacteria having V-ATPase, and therefore, the inhibitor improves the environment in the intestine so that good bacteria can easily grow.

In this regard, it is considered that VRE infection, enteritis due to *Clostridium difficile*, and the like are often caused by the disturbance of intestinal bacterial flora due to administration of antibiotics. Abnormalities in the immune system or intestinal bacterial flora in the intestinal tract may induce an autoimmune disease. Deterioration of the intestinal environment is considered to lead to large intestinal cancer or liver cancer, and the intestinal bacterial flora is deeply involved in a lifestyle-related disease such as obesity or diabetes. Accordingly, the inhibitor for V-ATPase activity according to the present invention adjusts the balance between the good bacteria and the bad bacteria in the intestinal bacterial flora, and is useful as a medicine for prevention or treatment of various diseases.

The inhibitor for V-ATPase activity according to the present invention (antibacterial agent, or bacterial flora control agent) is useful as an active component in a drug such as a medicine, or an agricultural chemical, and in particular, is preferably used for a medicine. Examples of the dosage form of medicine include a tablet, a capsule, a pill, powder, granules, fine granules, a jelly, and a liquid.

The concentration of the inhibitor for V-ATPase activity to be contained in a medicine may be appropriately determined, and is, for example, within the range of 1 μM to 100 mM, and preferably within the range of 100 μM to 10 mM. The inhibitor for V-ATPase activity may be used by dissolving the inhibitor in a solvent such as water, or may be used in a state of powder.

The above medicine may contain an additive such as a solvent, an excipient, a binding agent, a disintegrant, a lubricating agent, a stabilizer, or a suspending agent within the range of not impairing the effects of the present invention, in addition to the inhibitor for V-ATPase activity according to the present invention (antibacterial agent, or bacterial flora control agent). Examples of the solvent for pharmaceutical preparation include water, ethanol, and glycerin. Examples of the excipient include lactose, white soft sugar, glucose, mannitol, sorbitol, corn starch, potato starch, α-starch, dextrin, carboxymethyl starch, crystalline cellulose, hydroxypropyl methyl cellulose, carboxymethyl cellulose, carboxymethyl cellulose calcium, gum arabic, dextran, pullulan, silicates, calcium phosphate, calcium carbonate, and calcium sulfate. Examples of the silicates include light anhydrous silicic acid, synthetic aluminum silicate, and magnesium aluminometasilicate. Examples of the binding agent include gelatin, a polyvinyl pyrrolidone, and macrogol. Examples of the disintegrant include croscarmellose sodium, sodium carboxymethyl starch, and a cross-linked polyvinyl pyrrolidone. Examples of the lubricating agent include talc, stearic acid, calcium stearate, magnesium stearate, colloidal silica, Veegum, beeswax, spermaceti, boric acid, glycol, fumaric acid, adipic acid, sodium benzoate, sodium sulfate, leucine, sodium lauryl sulfate, magnesium lauryl sulfate, silicic anhydride, and silicic acid hydrate. Examples of the stabilizer include methylparaben, propylparaben, chlorobutanol, benzyl alcohol, phenylethyl alcohol, benzalkonium chloride, phenol, cresol, thimerosal, acetic anhydride, and sorbic acid. Examples of the suspending agent include polysorbate 80, and sodium carboxymethyl cellulose.

4. Screening Method

Next, a screening method for selecting a candidate compound for an inhibitor for $Na^+$-translocating V-ATPase activity from test compounds will be described. The screening method according to the present invention includes the following (a) Primary screening process and (b) Secondary screening process.

(a) Primary Screening Process

In the primary screening process, only a compound showing ATPase inhibitory activity is selected from a large number of compounds. First, test compounds having V-ATPase inhibitory activity are selected from a chemical library or the like. As the chemical library, a compound database owned by a university or the like can be used.

Next, each of the selected compounds is reacted with V-ATPase, and the ATPase activity is measured to evaluate whether or not the compound inhibits the ATPase. The ATPase activity can be measured by a molybdenum blue method for measuring absorbance of the inorganic phosphoric acid generated by hydrolysis of ATP. As the reaction conditions, conditions for measuring the ATPase activity can be adopted. As the buffer solution used in the reaction, Tris-HCl buffer can be used. The reaction time is usually 10 to 60 minutes, but can be appropriately adjusted depending on the air temperature or the like. The reaction of V-ATPase is terminated with the addition of a surfactant such as sodium dodecyl sulfate (SDS), and into which a color-developing liquid (such as ferrous sulfate) is added to give a color, and then the concentration of the inorganic phosphoric acid can be calculated by the measurement of the absorbance at a wavelength of 650 nm.

From the concentration of inorganic phosphoric acid calculated above, the inhibition rate of the V-ATPase reaction can be calculated. That is, a graph is created in which the inhibition rate is plotted on the vertical axis and the concentration of compound is plotted on the horizontal axis, and the concentration ($IC_{50}$) at which the inhibition rate becomes 50% is determined. As the concentration of compound at which $IC_{50}$ is obtained becomes lower, a higher V-ATPase inhibitory effect is exerted with a small amount, and accordingly, the compound can be taken as a candidate compound for the inhibitor for V-ATPase activity. In Examples to be described later, a compound with an $IC_{50}$ of less than 10 μM (hereinafter, referred to as "IC50<10 μM") is taken as a candidate compound selected in the primary screening process.

(b) Secondary Screening Process

The secondary screening process is a process of confirming whether or not the compound narrowed down in the primary screening process inhibits the growth of microorganisms. The secondary screening process includes at least a step (b-1) of untreated evaluation, a step (b-2) of treated evaluation, and a step (b-3) of candidate compound identification.

Step (b-1) of Untreated Evaluation

In the step of untreated evaluation, the living state of bacteria having V-ATPase is evaluated at a first pH and a second pH on the alkaline side of the first pH without bringing a test compound into contact with the bacteria. The V-ATPase is often expressed in microorganisms that grow under an alkaline environment. For this reason, in the present step, the growth state is confirmed by allowing microorganisms to grow under two environments of a specific pH (first pH) and a pH (second pH) on the alkaline side of the first pH. In a case where enterococci are subjected, it is preferable that the first pH is appropriately selected within the range of pH≤7.0, and the second pH is appropriately selected within the range of pH>7.0. For example, the first pH is set to pH 7.0, and the second pH is set to pH 8.0, or the like.

The culture conditions (culture medium, and culture temperature) of microorganisms in the step of untreated evaluation can be appropriately determined depending on the species of microorganism. For example, in a case where the microorganisms are enterococci, it is preferable to culture the microorganisms in a liquid medium containing a tryptone-yeast extract, and glucose or the like may be added to the medium as needed. As to the pH of the culture media to be used, the values of the first pH and the second pH are different from each other. Further, the culture temperature for enterococci is preferably 30 to 37° C.

The growing condition of microorganisms can be evaluated by confirming the number of the microorganisms. The number of the microorganisms can be confirmed by, for example, a method for measuring the absorbance of the culture medium in which the microorganisms are cultured, or a method for counting the number of microorganisms by culturing the microorganisms in a plate or the like. In a case of enterococci, the growing condition can be evaluated by measuring the absorbance at a wavelength of 600 nm ($OD_{600}$).

Step (b-2) of Treated Evaluation:

Next, a test compound is brought into contact with bacteria, and then the living states of bacteria at a specific pH (first pH) and a pH (second pH) on the alkaline side of the first pH are evaluated in a similar manner as in the step (b-1). The culture of microorganisms and the evaluation of growing condition are conducted under the same conditions and by the same method, as in the step (b-1).

Step (b-3) of Candidate Compound Identification:

Next, comparing between the living states of microorganisms in the step (a) of untreated evaluation and in the step (b) of treated evaluation, a test compound having a difference between the states is specified as a candidate compound for the antibacterial agent for bacteria. If the growth of microorganisms is more suppressed at a pH on the alkaline side of a specific pH in the step (b) of treated as compared with the step (a) of untreated, the test compound is determined to have a possibility of suppressing the V-ATPase activity, and is taken as a candidate compound for the inhibitor for V-ATPase activity. On the other hand, if the growth of microorganisms is suppressed even at a specific pH, the microorganisms more grow at a pH on the alkaline side of a specific pH in the step (b) of treated as compared with the step (a) of untreated, or the microorganisms grow to nearly the same extent in both steps, the test compound is determined not to affect the V-ATPase activity, and excluded as a candidate compound for the inhibitor for V-ATPase activity.

EXAMPLES

Hereinafter, the present invention will be specifically described by way of Examples, but these Examples do not limit the content of the present invention. Further, in the following Examples, the expression "%" is on a mass basis (mass percent) unless otherwise particularly specified.

(1) Preparation of Compound and V-ATPase (a) Obtaining Compound

Compounds as candidates for an inhibitor for V-ATPase activity were obtained from a chemical library of Drug Discovery Initiative, The University of Tokyo. Around 70000 kinds of compounds were obtained, and all of the compounds were subjected to primary screening by the ATPase activity measurement to be described later.

(b) Preparation of V-ATPase

The V-ATPase was prepared by the method disclosed in the following papers.

Paper 1: Takeshi Murata, et. al, "Purification and Reconstitution of $Na^+$-translocating Vacuolar ATPase from *Enterococcus hirae*", J. Biol. Chem. 272, 24885-24890 (1997)

Paper 2: Takeshi Murata, et. al, "Torque Generation of *Enterococcus hirae* V-ATPase", J. Biol. Chem. 289, 31212-31223 (2014)

(2) ATPase Activity Measurement (Primary Screening)

ATPase activity measurement was conducted by a molybdenum blue method that quantifies the inorganic phosphoric acid generated by hydrolysis of ATP with the use of absorbance measurement. The measurement was conducted in a 96-well plate, and 0.05% DDM (n-dodecyl-β-D-maltoside), 10 μg/mL of V-ATPase (purified from enterococci or recombinant *E. coli*), and 20 μM of a compound were added into a buffer (100 mM Tris-HCl at pH 8.5, 100 mM NaCl, 5 mM $MgSO_4$, 10% glycerol). Into the mixture obtained above, ATP was added so as to be 5 mM, the whole amount was set to 100 μL, the reaction was started while stirring the mixture with a stirrer, and the reaction time was set to 30 minutes. Since the ATPase activity changes largely depending on the reaction temperature, the reaction time was adjusted within the range of 10 to 60 minutes corresponding to the air temperature on the day of the experiment. With the addition of 50 μL of 20% SDS, the V-ATPase was denatured and the reaction was terminated, and into the resultant mixture, 75 μL of color-developing liquid (5% ferrous sulfate, 1.6% ammonium molybdate, and 1 M sulfuric acid) was added to give a color. Immediately, the absorbance at a wavelength of 650 nm was measured by using a plate reader. Four kinds of $KH_2PO_4$ aqueous solutions of 0.2 mM, 0.5 mM, 1.0 mM, and 1.5 mM were reacted with MQ (ultrapure water) in the same experiment system, and then the activity of V-ATPase was measured by determining the concentration of generated inorganic phosphoric acid with the use of a created calibration curve. In this regard, a compound that had inhibited 50% or more of the activity of V-ATPase was diluted stepwisely so as to have a concentration of 10 μM, 5 μM, 2 μM, 1 μM, 500 nM, 200 nM, 100 nM, and 50 nM, and the measurement similar to the above was conducted.

(3) Results of Primary Screening

Figure 2:
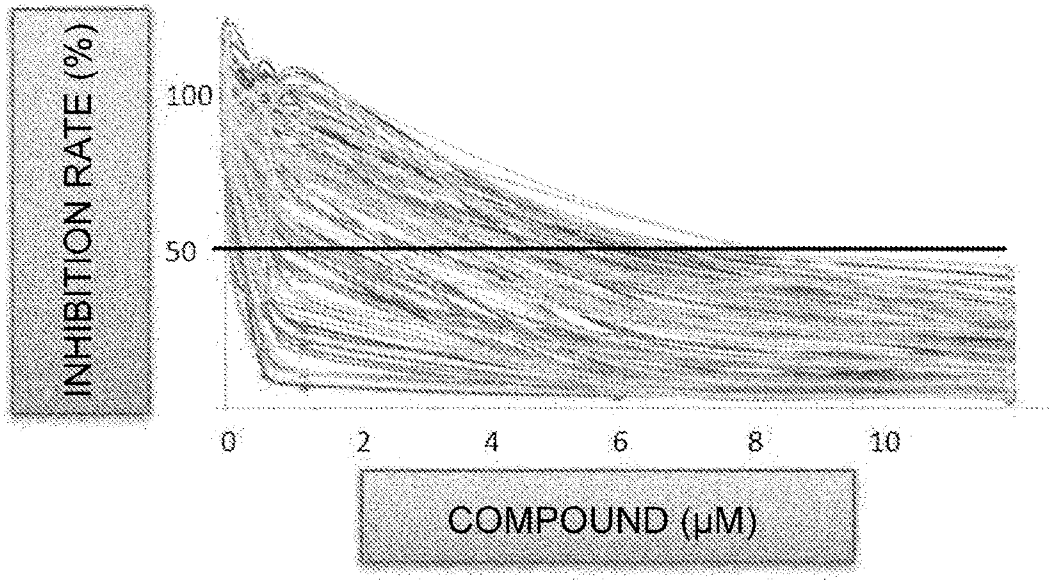
FIG. 2 is a graph showing the inhibition rate of V-ATPase activity by a candidate compound and the compound concentration.

From the results of the above measurement of ATPase activity, the inhibition rate was calculated comparing the decrease in the activity by assuming the activity under the condition of no compound addition as 100. A graph was created in which the inhibition rate was plotted on the vertical axis and the concentration of compound was plotted on the horizontal axis (FIG. 2). From the graph, the concentration ($IC_{50}$) of compound at which the inhibition rate becomes 50% was determined. As a result, there were 280 kinds of compounds with an $IC_{50}$ of less than 10 μM ($IC_{50}$<10 μM), and 12 kinds of compounds with an $IC_{50}$ of less than 100 nM ($IC_{50}$<100 nM). As a result of verifying the effect of 280 kinds of compounds with $IC_{50}$<10 μM on human-derived HeLa cells, 24 kinds of compounds showed toxicity, and 256 kinds excluding the 24 kinds of compounds were taken as candidate inhibitors. From these 256 kinds of compounds, 24 kinds of compounds were selected in consideration of the compounds having higher activity and the diversity. The structural formulas of these 24 kinds of compounds are shown below.

[Chemical formula 18]

(V-6)

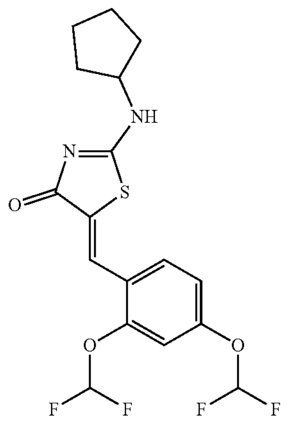

(V-27)

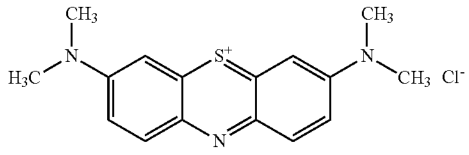

(V-84)

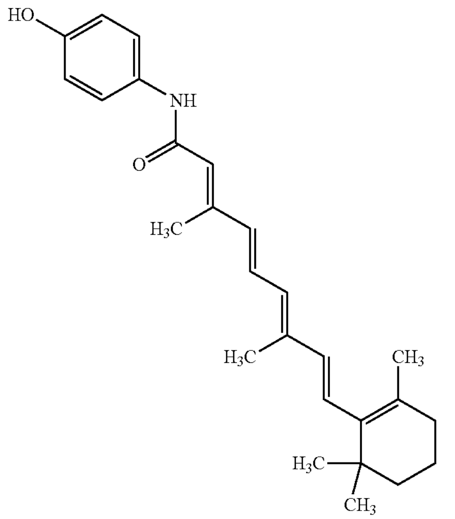

-continued
(V-85)
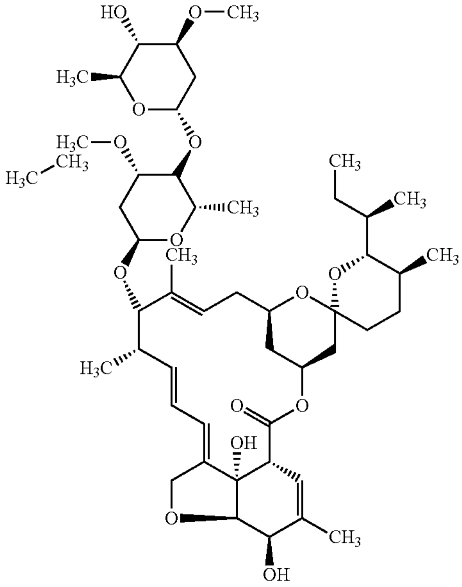
(V-91)
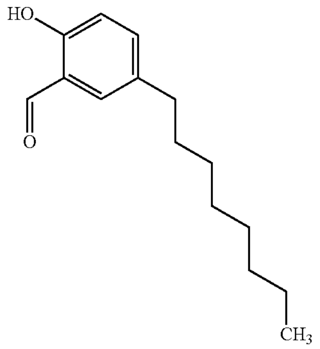
(V-99)
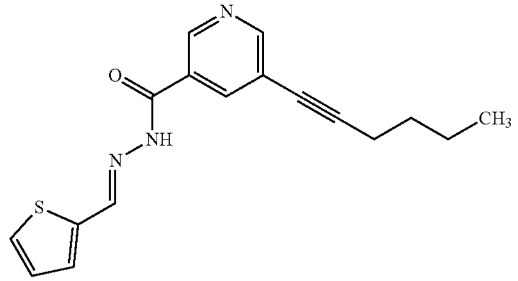
[Chemical formula 19]
(V-103)
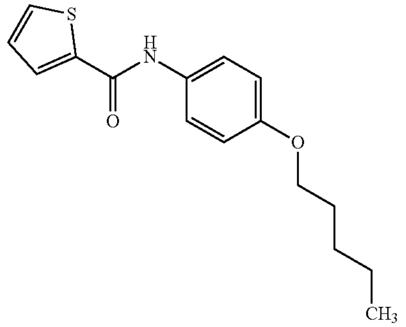
-continued
(V-105)
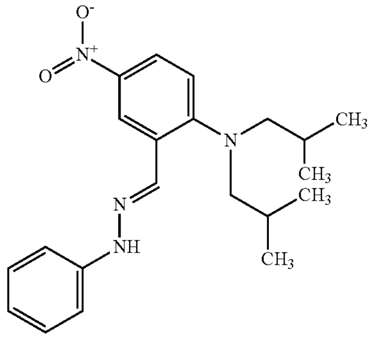
(V-115)
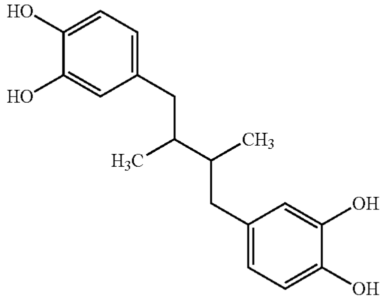
(V-124)
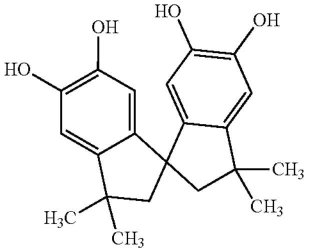
(V-130)
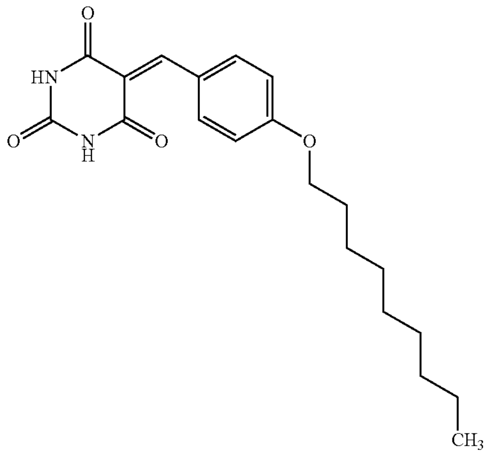

-continued
(V-149)
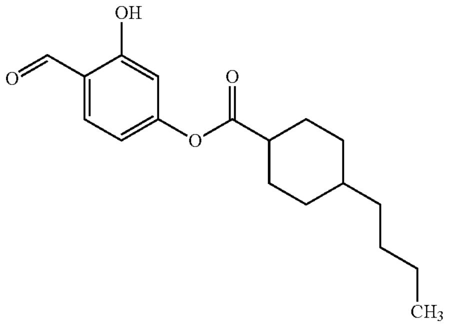
[Chemical formula 20]
(V-150)
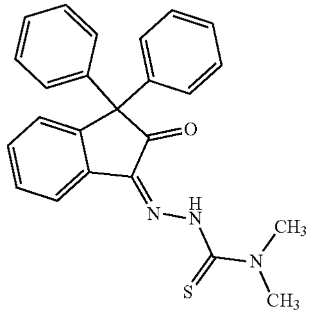
(V-153)
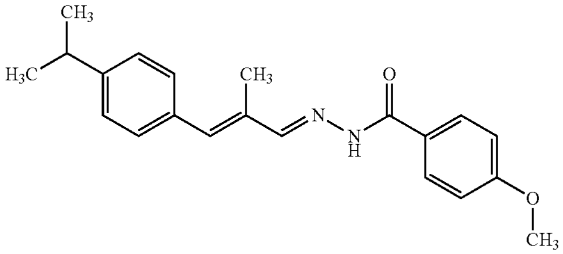
(V-157)
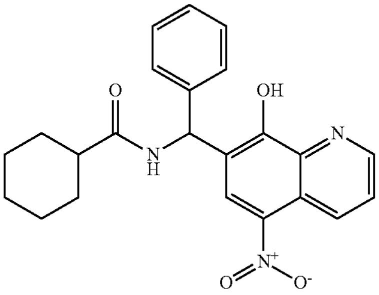
(V-161)
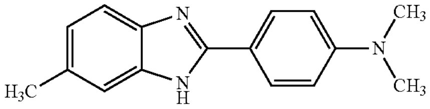
(V-170)
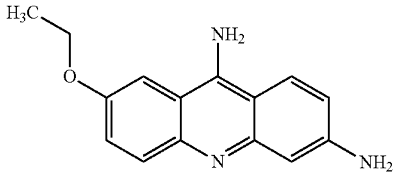
-continued
(V-171)
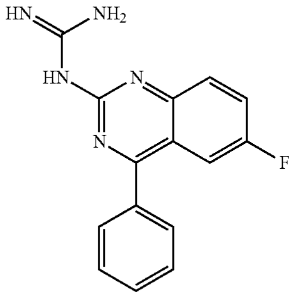
[Chemical formula 21]
(V-189)
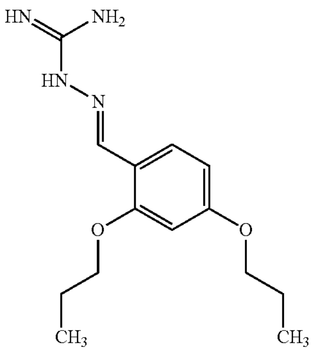
(V-201)
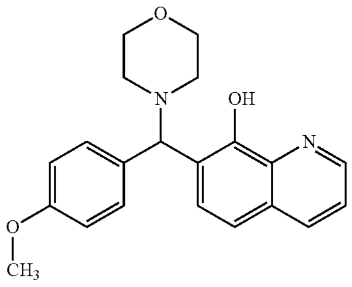
(V-207)
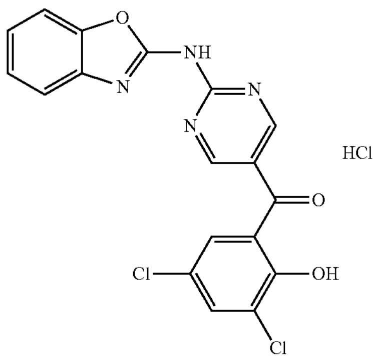

-continued (V-234)

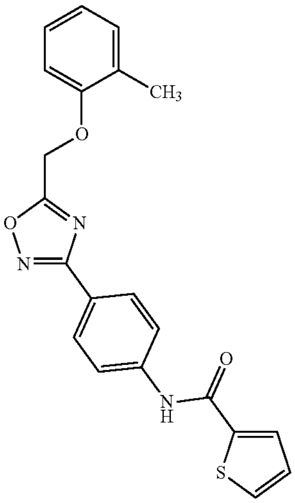

(V-278)

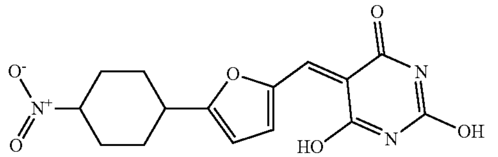

(V-289)

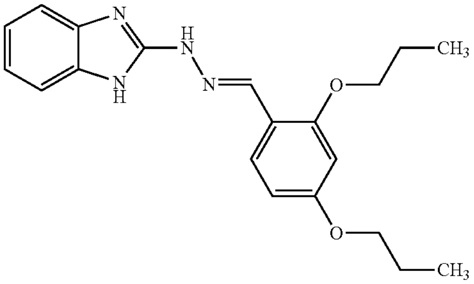

The above-described 24 kinds of compounds were subjected to secondary screening by the following growth experiment of enterococci.

(4) Growth Experiment (Secondary Screening) of Enterococci

In the culture of enterococci (*Enterococcus hirae*), a culture medium in which the $Na^+$ concentration had been adjusted by adding a buffer solution using 2% tryptone and 1% yeast extract as the base was used. In a case of adding glucose, glucose prepared in a 50% solution was added so as to be 1% into the culture medium when the culture medium was used. The whole amount 200 μL was cultured using a 96-well plate, and $OD_{600}$ was measured every hour by using a plate reader. By using culture media at pH 7.0 and pH 8.5, the effect of pH on the growth was observed. In culture of bacteria, the pH often fluctuates largely due to the decomposition of the sugars required for the growth, and it is extremely important to maintain a constant pH in this experiment, and therefore, the pH was maintained constant with the addition of a buffer suitable for each pH. Since the V-ATPase is expressed only under an alkaline condition, the growth inhibition observed with the addition of an inhibitor is largely dependent on the pH. Further, the inhibitor does not affect the growth of bacteria that have no V-ATPase.

(5) Results of Secondary Screening $IC_{50}$ and the like of the above 24 kinds of compounds are described in the following table. In this regard, the symbol "+" in the column of "Specificity" in the following table indicates that there was no growth inhibition at pH 7.0 but was the growth inhibition at pH 8.5, the symbol "–" indicates that there was no growth inhibition in any case, and the symbol "n.a." indicates that there was the growth inhibition in any case. Specifically, with respect to the symbol "+", a compound having a growth inhibition rate of 20% or less at pH 7.0 is determined that there was no growth inhibition. Further, with respect to the symbol "–", a compound having a growth inhibition rate of 20% or less at both pH 7.0 and pH 8.5 is determined that there was no growth inhibition. Furthermore, with respect to the symbol "n.a.", a compound having a growth inhibition rate of 60% or more at pH 7.0 is determined that there was the growth inhibition. In addition, the growth inhibition rate of a compound having no clear inhibition is also recorded for reference.

TABLE 2

| Examples, etc. | Compound | Molecular weight (MW) | $IC_{50}$ (nM) | Growth inhibition rate (%) | Specificity |
|---|---|---|---|---|---|
| Example 1 | V-6 | 404.379 | 80 | 77.9 | + |
| Reference Example 1 | V-27 | 319.852 | 3000 | 64.0 | + |
| Example 2 | V-84 | 391.5457 | 80 | 90.6 | – |
| Reference Example 2 | V-85 | 875.0928 | 10000 | 66.4 | + |
| Reference Example 3 | V-91 | 234.334 | 850 | 90.9 | n.a. |
| Reference Example 4 | V-99 | 311.401 | 2500 | 6.7 | – |
| Reference Example 5 | V-103 | 289.393 | 100 | 45.3 | + |
| Reference Example 6 | V-105 | 368.4726 | 1000 | 90.8 | n.a. |
| Reference Example 7 | V-115 | 302.3649 | 400 | 0.3 | – |
| Reference Example 8 | V-124 | 340.4129 | 300 | 49.2 | + |
| Example 3 | V-130 | 358.4314 | 20 | 88.2 | – |
| Reference Example 9 | V-149 | 304.3808 | 4500 | 90.5 | n.a. |
| Reference Example 10 | V-150 | 399.508 | 500 | 70.4 | n.a. |
| Reference Example 11 | V-153 | 336.4275 | 1000 | 13.3 | – |
| Reference Example 12 | V-157 | 405.4464 | 2000 | 84.2 | n.a. |
| Example 4 | V-161 | 251.3263 | 85 | 88.7 | + |
| Reference Example 13 | V-170 | 253.2991 | 10000 | 49.7 | + |
| Reference Example 14 | V-171 | 281.2877 | 2500 | 85.6 | + |
| Reference Example 15 | V-189 | 278.3501 | 4500 | 91.2 | + |
| Reference Example 16 | V-201 | 350.411 | 4000 | 19.6 | – |
| Reference Example 17 | V-207 | 437.664 | 5000 | 12.0 | – |
| Example 5 | V-234 | 391.45 | 40 | 75.5 | + |
| Reference Example 18 | V-278 | 327.2485 | 250 | 44.4 | + |
| Reference Example 19 | V-289 | 352.4302 | 600 | 55.0 | + |

Figure 3:
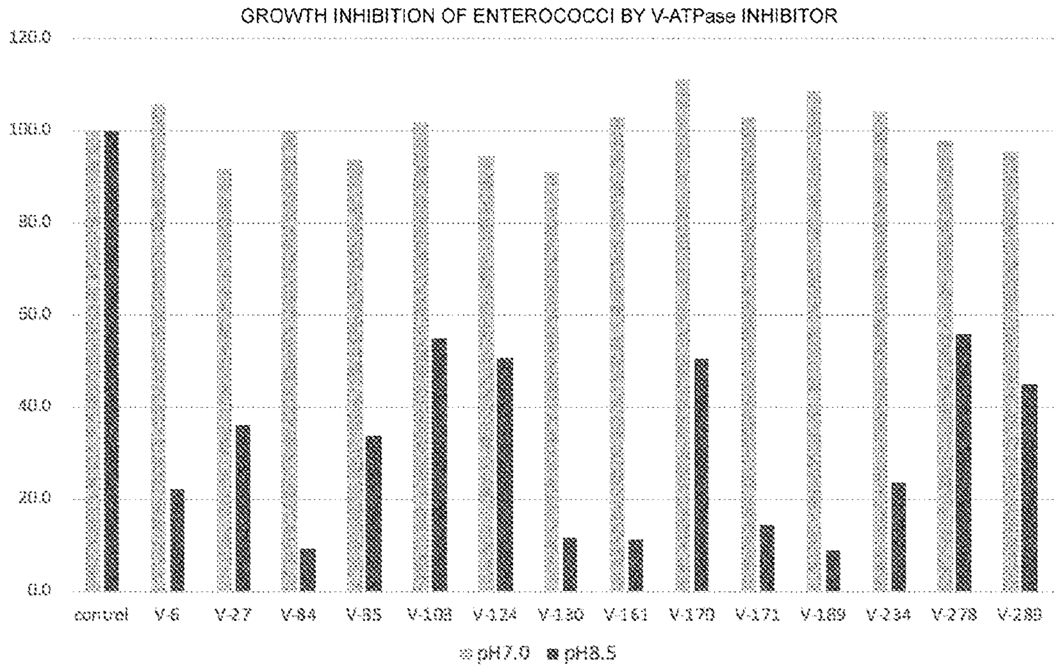
FIG. 3 is a graph showing the results of growth experiments of enterococci by candidate compounds.

Further, among them, for 14 kinds of compounds having "+" in the column of "Specificity", the growth results are shown in a graph (FIG. 3). The horizontal axis shows the candidate compounds, and the vertical axis shows the number (%) of bacteria measured by absorbance. A control is shown on the extreme left of the graph, and in the control and each candidate compound, the bar on the left side shows the result in the culture condition at pH 7.0, and the bar on the right side shows the result in the culture condition at pH 8.5. As shown in this graph, it can be understood that the growth of enterococci at pH 8.5 is suppressed as compared with that at pH 7.0 in any one of the candidate compounds.

Among the above 14 kinds of compounds, 3 kinds of compounds, which have a high affinity for V-ATPase ($IC_{50}$<=400), a high growth inhibitory effect (growth inhibition rate (%)>=70%), and further no non-specific inhibition, were specified as compounds showing an inhibitor for V-ATPase activity having high inhibitory efficiency. Specifically, compounds of Example 1 (V-6), Example 4 (V-161), and Example 5 (V-234) were specified. In particular, the compound (2-phenyl benzimidazole derivative) of Example 4 (V-161), is considered to be a most useful candidate compound, from the results of $IC_{50}$ and growth inhibition. Further, 2 kinds of compounds (Example 2 (V-84) and Example 3 (V-130), which have a high affinity for V-ATPase ($IC_{50}$<=400), a high growth inhibitory effect (growth inhibition rate (%)>=70%), and non-specific inhibition, were also specified as candidate compounds.

(6) Co-Crystallization and X-Ray Crystal Structure Analysis

The compound of Example 4 (V-161) and the c ring of V-ATPase were co-crystallized, and an X-ray crystal structure analysis was performed. The V-ATPase derived from enterococci was expressed in recombinant *E. coli* by using the methods disclosed in the above papers 1 and 2, and purified into a complex, and then the c ring was isolated. The c ring was adjusted to be 2 mg/mL, and V-161 was added so as to be 500 μM. The crystallization was performed at 23° C. under the conditions of 100 mM Tris-HCl at pH 8.0, 220 mM sodium citrate, and 32% PEG400. The obtained crystal was subjected to an X-ray diffraction experiment at the beamline of a photon factory (PF), which is a synchrotron radiation facility. Analysis was performed from the diffraction image, and the structure was determined at a resolution of 2.3 Å. The results are shown in FIGS. 4 and 5.

In this regard, for the detail method of X-ray crystal structure analysis, the following paper regarding X-ray crystal structure analysis of the c ring of *Enterococcus* V-ATPase can be referred.

Paper 3: Takeshi Murata, et. al, "Structure of the Rotor of the V-Type $Na^+$-ATPase from *Enterococcus hirae*" Science 308, 654-659 (2005)

Figure 4A:
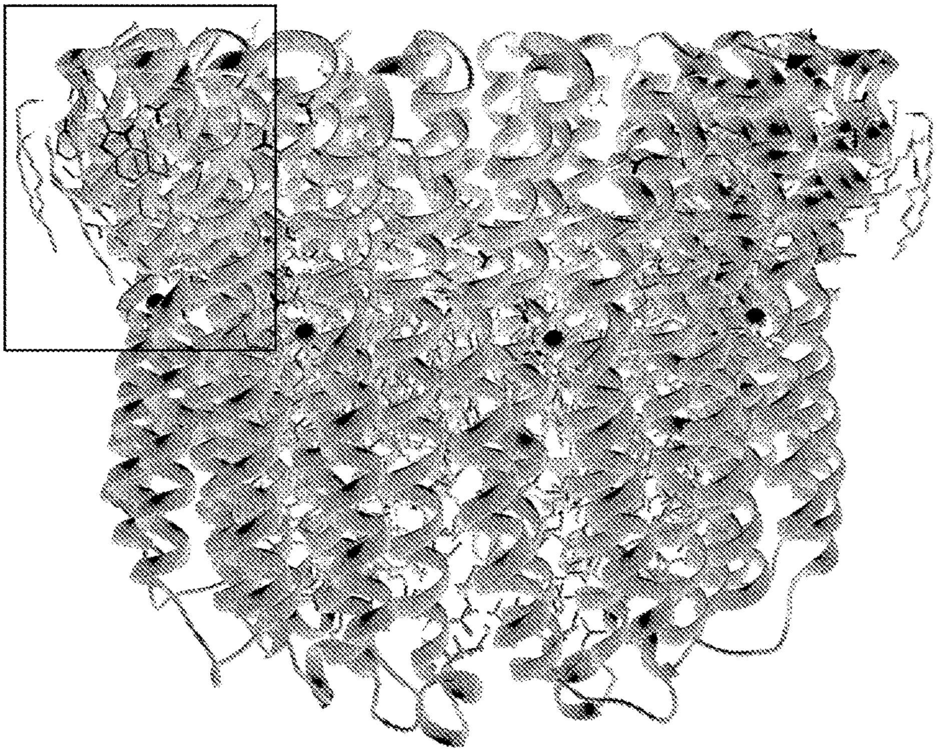
FIG. 4A is dimensional structures showing a state in which an inhibitor for V-ATPase activity binds to the c ring of V-ATPase.
Figure 4B:
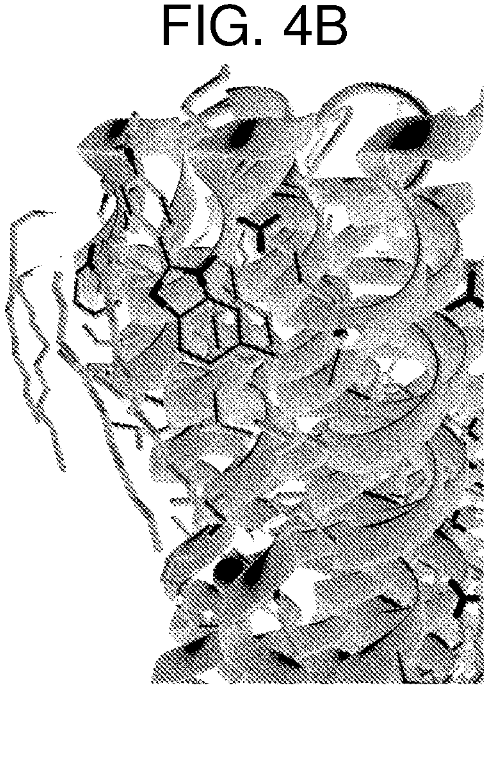
FIG. 4B is an enlarged view of the portion surrounded by the square in FIG. 4A.
Figure 5:
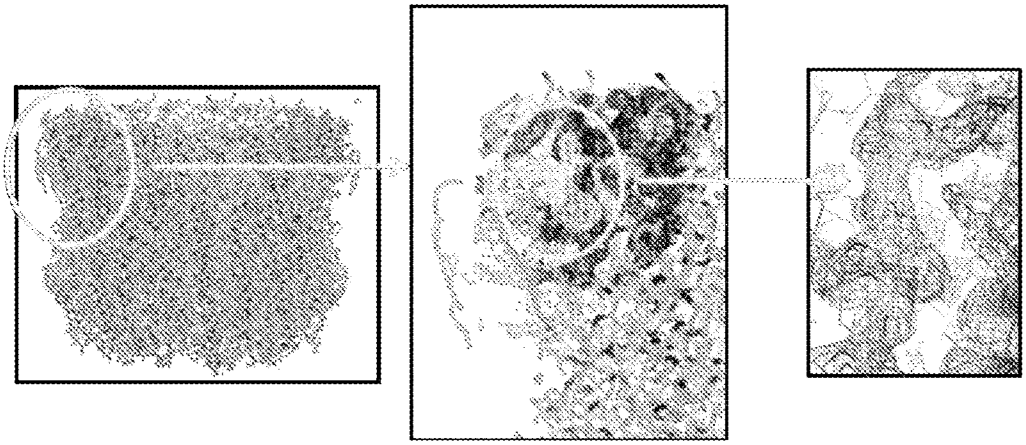
FIG. 5 is diagrams showing the result of X-ray crystal structure analysis of the compound of Example 4 and the c ring of V-ATPase.

As shown in FIG. 4A, the ribbon-like shape indicates a helix of the c ring, the stick-like shape around the helix indicates lipid molecules and surfactant molecules, and the grains in the central portion indicate sodium ions. FIG. 4B is an enlarged view of a portion surrounded by the square in FIG. 4A. Further, FIG. 5 shows electron density maps, the map on the left side shows the overall structure of c ring, and the maps in the middle and on the right side show structures of binding site of V-161, which are gradually enlarged structures. From these structures, it was found that the V-161 interacted with an amino acid residue around a portion containing the 52nd phenylalanine of the c ring, and was bound to the outer peripheral surface.

(7) Compound Development of 2-Phenyl Benzimidazole Derivative

Other 2-phenyl benzimidazole derivatives having a skeleton common to the V-161 were synthesized and developed. The compounds are the following 10 kinds of (V-161-01) to (V-161-10). The structural formulas of the compounds are shown below.

[Chemical Formula 22]

The inhibitory effect of these compounds on the ATPase activity was evaluated in the same manner as in "(2) ATPase activity measurement". The results are shown in the following table. In this regard, Reference Example 4-02 (V-161-06) had no specificity of the activity due to the pH (highly active at both pH 7.0 and pH 8.5), and Reference Example 4-05 (V-161-09) had no activity.

TABLE 3

| Examples, etc. | Compound | Molecular weight (MW) | $IC_{50}$ (nM) | Growth inhibition rate (%) | Specificity |
|---|---|---|---|---|---|
| Example 4 | V-161 | 251.33 | 85 | 88.7 | + |
| Example 4-01 | V-161-01 | 277.37 | 50 | 89.7 | + |
| Example 4-02 | V-161-02 | 236.32 | 120 | 88.5 | + |
| Example 4-03 | V-161-03 | 287.16 | 120 | 89.8 | + |
| Example 4-04 | V-161-04 | 334.16 | 120 | 90.3 | + |
| Reference Example 4-01 | V-161-05 | 364.19 | 500 | 87.5 | + |
| Reference Example 4-02 | V-161-06 | 362.21 | 600 | 85.5 | n.a. |
| Reference Example 4-03 | V-161-07 | 208.26 | 1000 | 76.2 | + |
| Reference Example 4-04 | V-161-08 | 194.24 | 2000 | 18.5 | + |
| Reference Example 4-05 | V-161-09 | 330.23 | No activity | – | – |
| Reference Example 4-05 | V-161-10 | 238.29 | 120 | 86.8 | + |

Among these results, 5 kinds of compounds of Examples 4-01 (V-161-01) to 4-04 (V-161-04) and Example 4-05 (V-161-10), which have a high affinity for V-ATPase ($IC_{50}$<=400), a high growth inhibitory effect (growth inhibition rate (%)>=70%), and further no non-specific bond, were specified as inhibitors of V-ATPase activity having high inhibitory efficiency. On the other hand, compounds of Reference Example 4-04 (V-161-08) and Reference Example 4-05 (V-161-09) had no inhibitory effect on the ATPase activity.

(8) Confirmation of Antibacterial Action Against Pathogenic Bacteria

It was confirmed whether the V161 showed the growth inhibition against pathogenic bacteria having V-ATPase similar to enterococci (*Enterococcus hirae*) in a similar manner as in the above "(4) Growth experiment of enterococci". As the pathogenic bacteria, *Enterococcus faecalis* and *Enterococcus faecium* that are vancomycin-resistant enterococci (VRE), and *Clostridium difficile* that leads to deterioration of intestinal environment and is resistant to multiple drugs were prepared. The VRE were cultured by using culture media at pH 7.0, pH 7.5, and pH 8.0, the *C. difficile* was cultured by using culture media at pH 6.5, pH 7.0, and pH 7.5, and the difference in the number of bacteria was confirmed by measuring $OD_{600}$. The results are shown in FIGS. 6 and 7.

Figure 6:
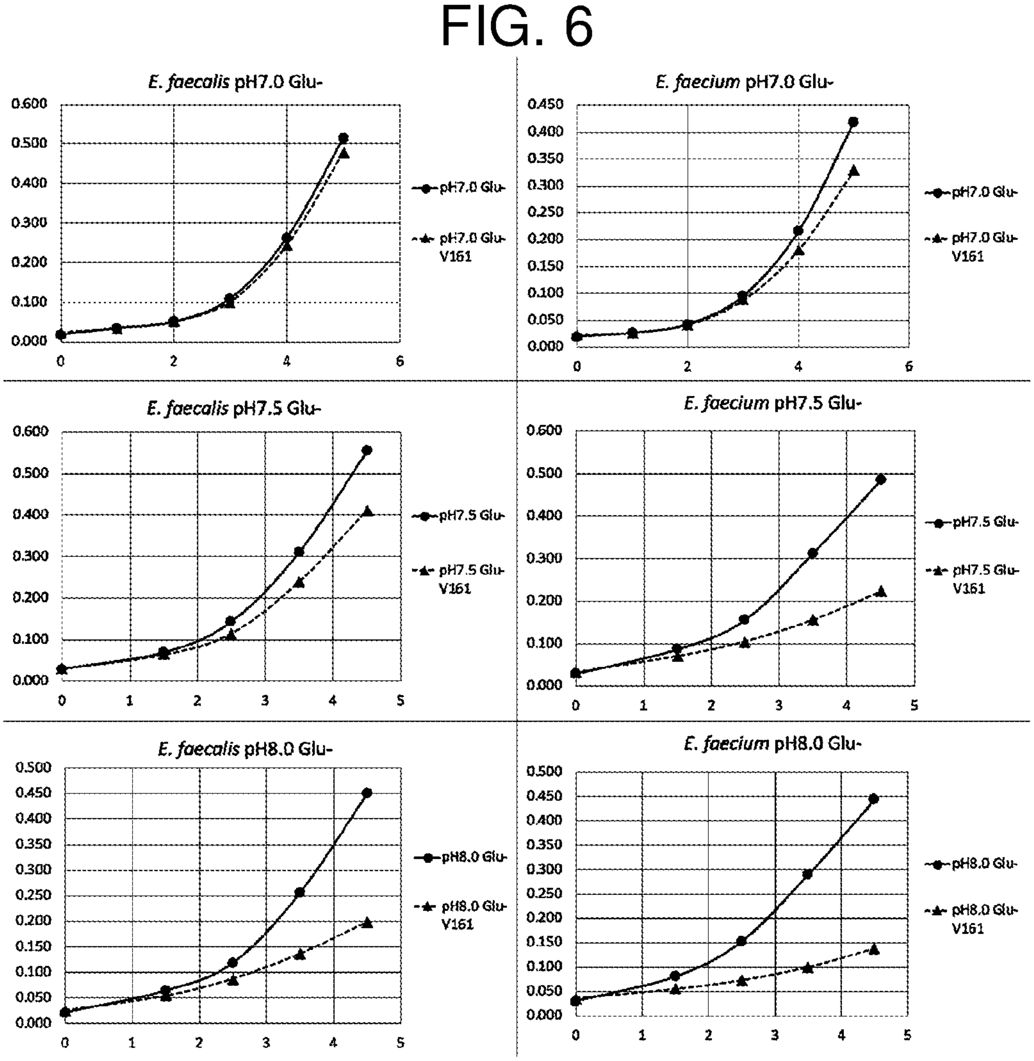
FIG. 6 is graphs showing the results of growth suppression tests of pathogens by using compounds of Example 4.
Figure 7:
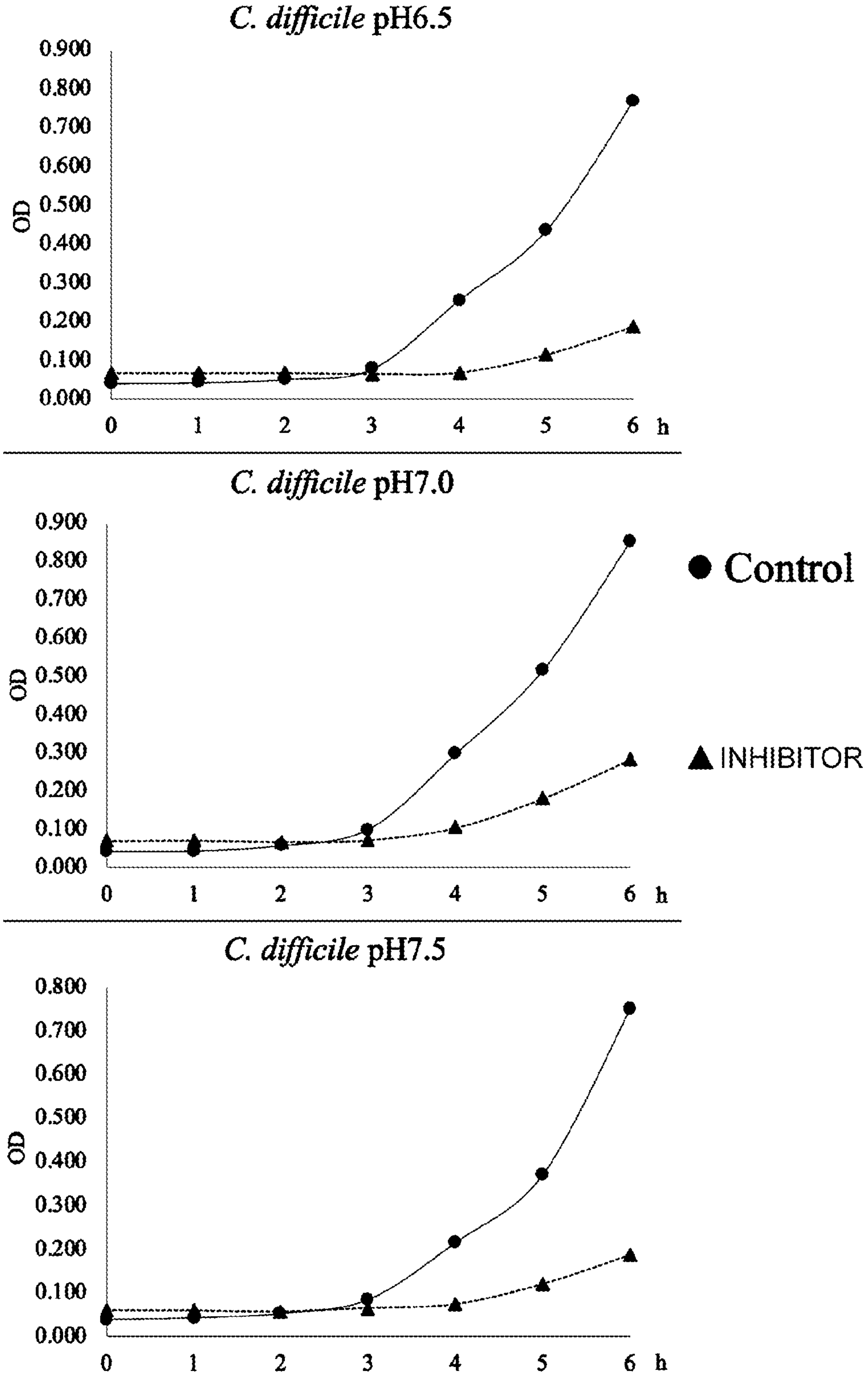
FIG. 7 is graphs showing the results of growth suppression tests of pathogens by using compounds of Example 4.

FIG. 6 shows results of vancomycin-resistant enterococci (VRE), and shows data of *E. faecalis* on the left side and data of *E. faecium* on the right side. The data of pH 7.0, pH 7.5, and pH 8.0 are shown in order from the top of FIG. 6. From FIG. 6, it was found that the growth of all pathogens was inhibited in a pH-dependent manner, and V-161 had a specific growth inhibitory activity under an alkaline condition due to the inhibition of V-ATPase activity. Further, it can be confirmed that *E. faecium* is more strongly affected by the V-161 than *E. faecalis* is. FIG. 7 shows data of pathogenic bacteria belonging to the genus *Clostridium*. The data of pH 6.5, pH 7.0, and pH 7.5 are shown in order from the top of FIG. 7. From FIG. 7, the growth of *C. difficile* was inhibited even under a neutral or acidic condition, and it was suggested that the pH range in which V-ATPase is expressed was large in the pathogenic bacteria belonging to the genus *Clostridium*, and the V-161 acted even under a neutral or acidic condition.

(9) Confirmation of Acting Condition of Intestinal Environment

Figure 8:
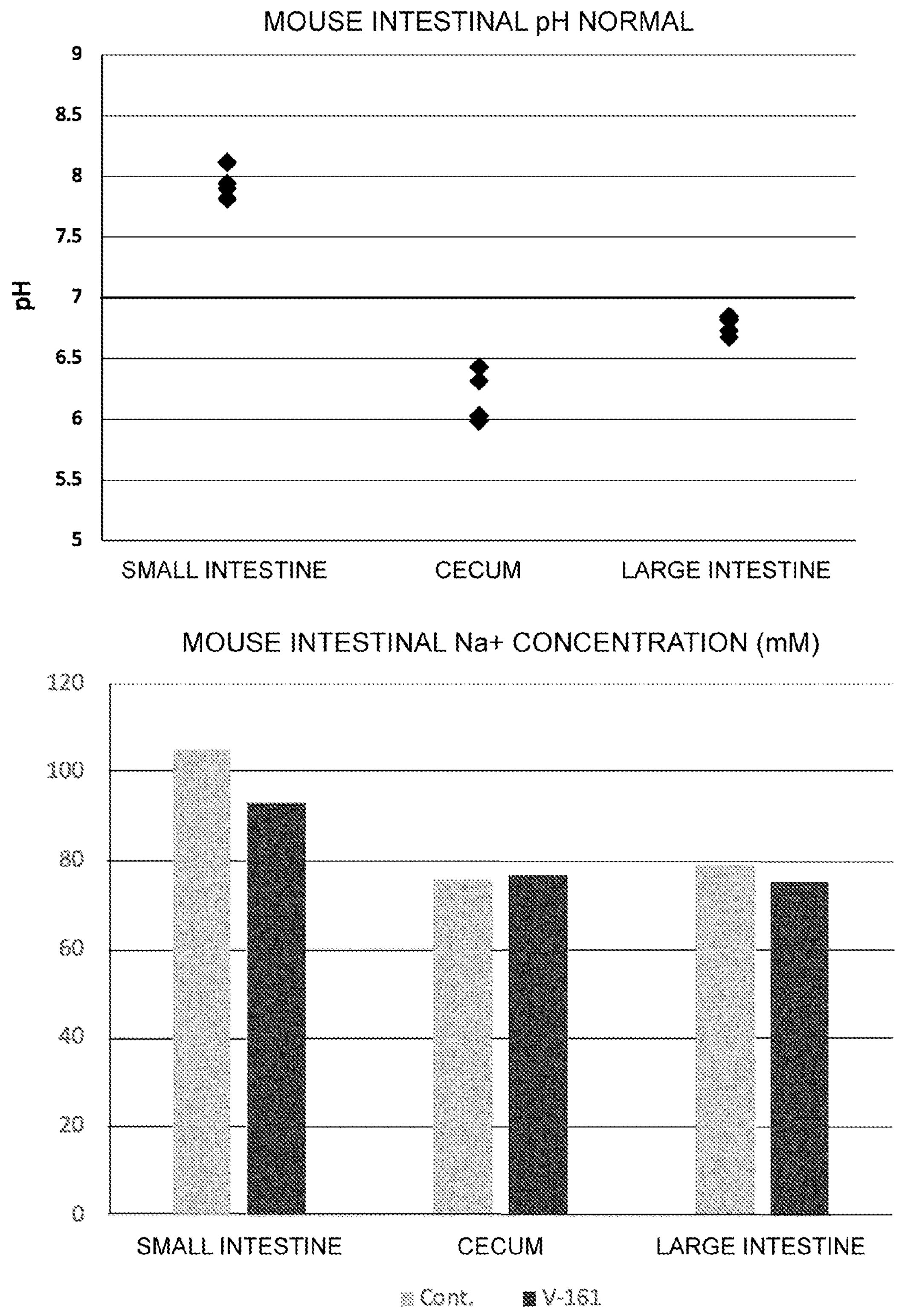
FIG. 8 is graphs showing the results of evaluation of influence on the intestinal environment by using the compounds of Example 4.

The effect of V-161 on the intestinal environment was examined by using mice (C57BL/6, female, aged 6 weeks, and weighed around 15 g). The V-161 was suspended in Soybean PC and Meylon so as to be 20 mM. To each of four mice, 0.5 ml of the suspension was orally administered once a day, and on five days after the start of administration, the mice were dissected and the feces and intestinal tract contents were collected, and the intestinal pH and sodium ion concentration were measured. The results are shown in FIG. 8. The upper part of FIG. 8 shows the intestinal pH, and the lower part shows the sodium ion concentration.

From the results, it was found that particularly in the small intestine, the pH environment was suitable for V-ATPase to be expressed and for V-161 to act. Further, in spite of the administration of a large amount of V-161, toxicity was not observed in the mice.

(10) Confirmation of Mouse Intestinal Environment (Administration of High-Protein Feed and Antibiotics)

On a high-protein diet, so-called bad bacteria increase and the intestinal environment is often disturbed, and administration of antibiotics causes a significant decrease of intestinal bacteria and often leads to colonization and infection of pathogens. From this point of view, two models were used for the verification.

Figure 9:
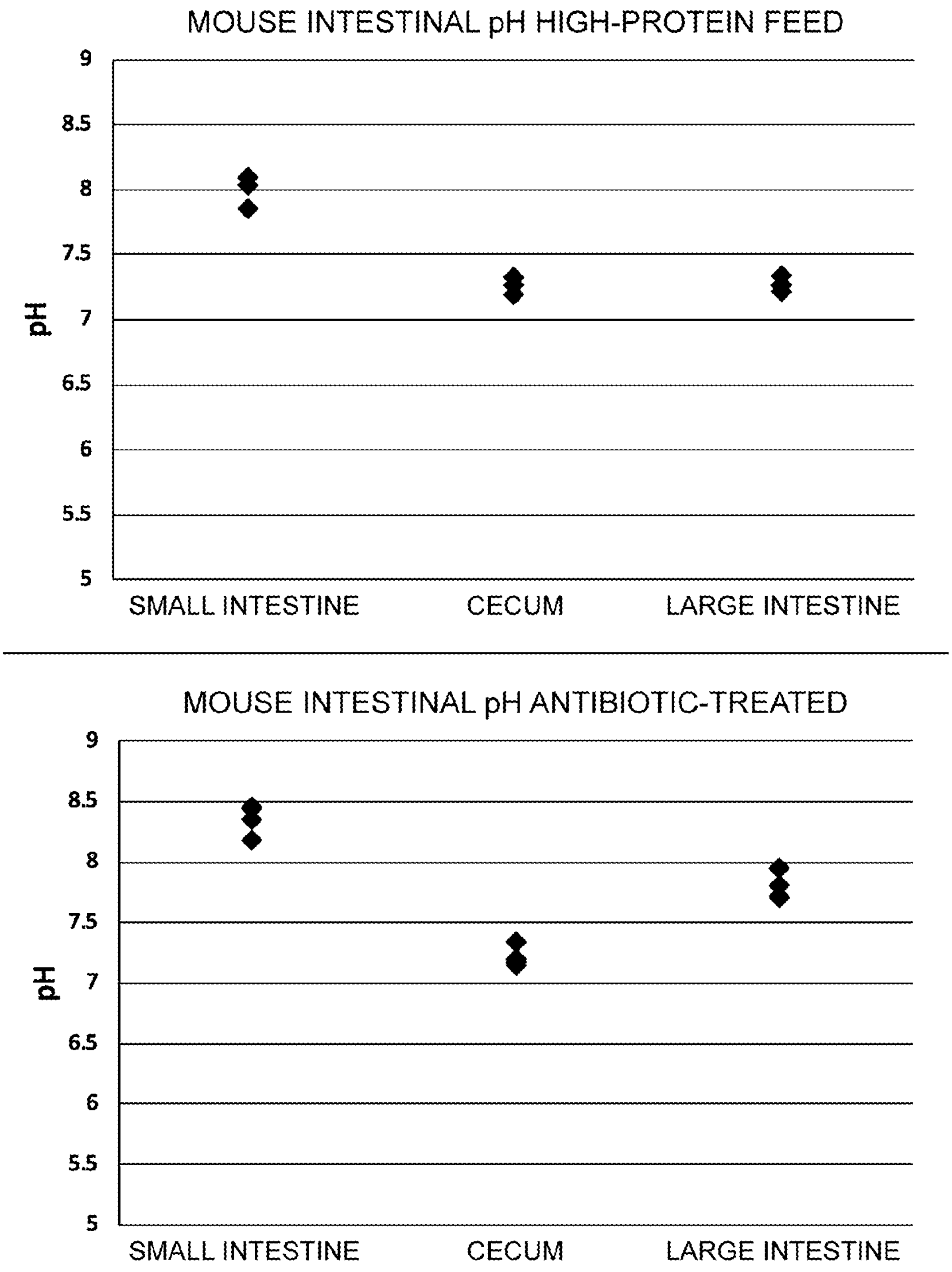
FIG. 9 is graphs showing the results of measurement of intestinal pH of the mice to which high-protein feed and antibiotics were administered.

First, three mice to which high-protein feed (protein 65%) was given and three mice to which normal feed (protein 25%) was given were prepared as models, respectively. Further, mice to which an antibiotic (ampicillin 1 g/L) in drinking water was administered and mice to which normal drinking water was administered were prepared as models, respectively. All of the mice as models were dissected one week later, the intestinal tract contents were collected, and the pH was measured. The results are shown in FIG. 9. The upper part of FIG. 9 shows the results of the mice to which the high-protein feed was given, and the lower part shows the results of the mice to which the antibiotic was administered.

In any of the models, it was able to be confirmed that the pH increased slightly in the small intestine, and the pH largely increased in the cecum and large intestine, and the normally acidic intestinal environment changed to alkaline. From these results, in the deteriorated intestinal environment, the pH tends to become higher, and it is presumed that the V-ATPase inhibitor is more likely to act in the higher-pH environment than in a normal environment.

(11) Test in VRE-Infected Mice

Figure 10:
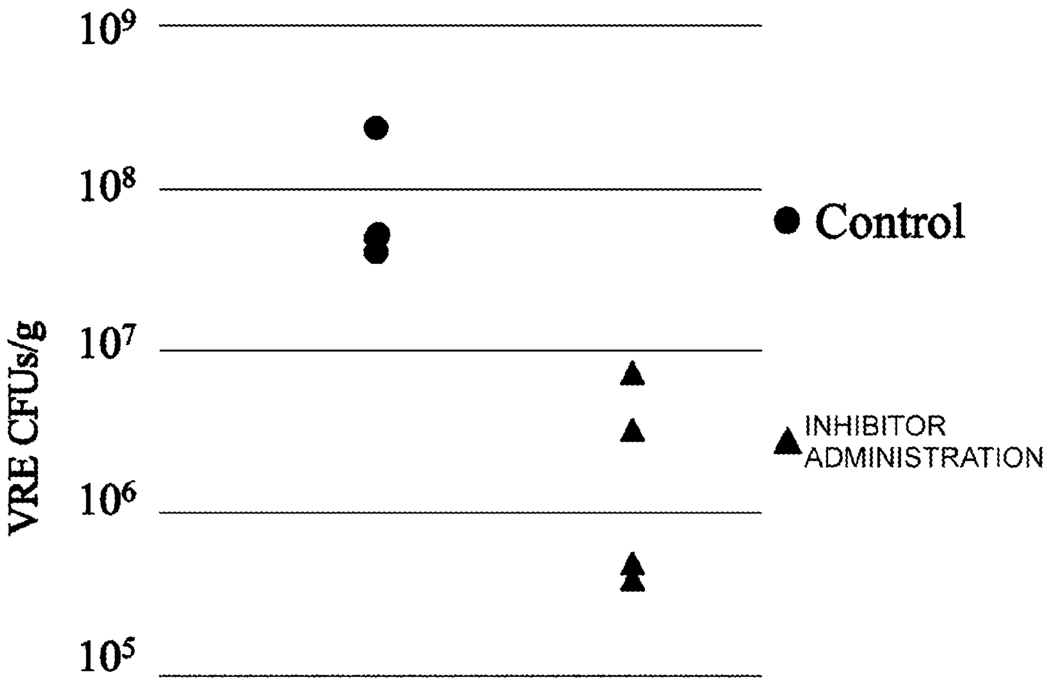
FIG. 10 is graphs showing the results of measurement of the number of vancomycin-resistant enterococci (VRE) of VRE-infected mice to which the compounds of Example 4 were administered.
Figure 10:
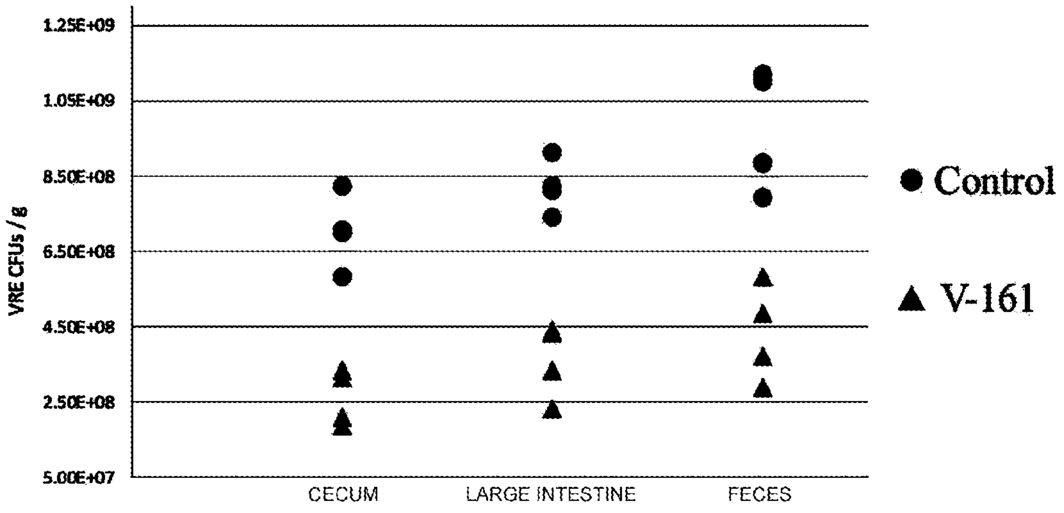

Mice treated with antibiotics were infected with *E. faecium* of VRE, and V-161 was administered to the mice. The experimental conditions such as the dose of antibiotics and V-161 were the same as those in "(9) Confirmation of acting condition of intestinal environment", and "(10) Confirmation of mouse intestinal environment (administration of high-protein feed and antibiotics)". The results are shown in FIG. 10. The upper part of FIG. 10 shows the results of the small intestine, and the lower part shows the results of the cecum, large intestine, and feces. In this regard, the vertical axis of FIG. 10 shows the number of live bacteria of VRE.

From FIG. 10, the VRE in the small intestine was remarkably decreased (97% decrease) in a case where V-161 was added as compared with the controls. Further, the VRE in the cecum, large intestine, and feces was significantly decreased (around 50% decrease) in any case where V-161 was added as compared with the controls. That is, it was found that the V-161 exerts a growth suppressive effect on the VRE in the intestine of mouse.

(12) (1,2,4-Oxadiazol-3-yl)phenyl Derivative

Other (1,2,4-oxadiazol-3-yl) phenyl derivatives having a skeleton common to V-234 were synthesized and developed. The compounds are the following 3 kinds of (V-234-01) to (V-161-03). The structural formulas of the compounds including V-234 are shown below.

[Chemical formula 23]

V-234

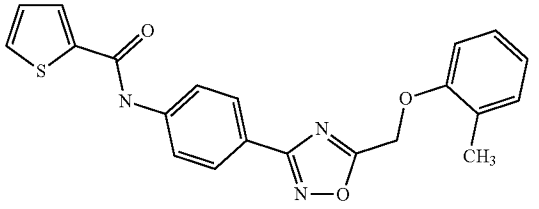

V-234-01

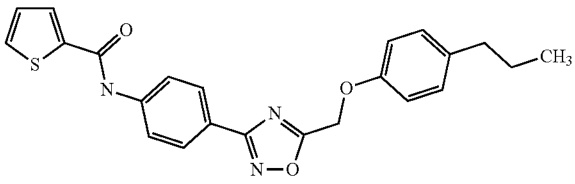

V-234-02

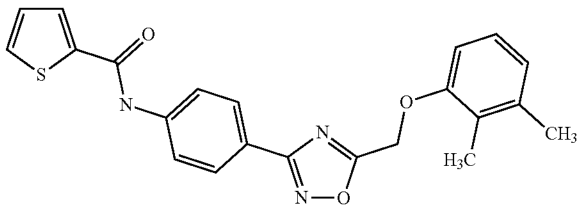

V-234-03

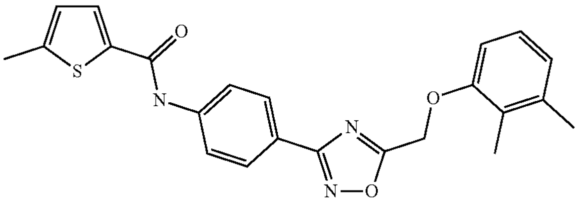

The inhibitory effect of these compounds on the ATPase activity was evaluated in the same manner as in "(2) ATPase activity measurement". The results are shown in the following table.

TABLE 4

| Examples, etc. | Compound | Molecular weight | $IC_{50}$ (nM) | Growth inhibition rate (%) |
|---|---|---|---|---|
| Example 5 | V-234 | 391.45 | 40 | 75.5 |
| Example 5-01 | V-234-01 | 419.50 | 50 | 76.9 |
| Example 5-02 | V-234-02 | 405.48 | 40 | 74.8 |
| Example 5-03 | V-234-03 | 419.50 | 6 | 72.0 |

The compounds of Examples 5-01 to 5-03 all had a high affinity for V-ATPase ($IC_{50}$<=400), a high growth inhibitory effect (growth inhibition rate (%)>=70%), and further no non-specific bond.

The invention claimed is:

1. A method of suppressing growth of a bacterium having V-ATPase in a subject, comprising the step of:

administering a medicine to the subject having bacterium having V-ATPase, wherein the medicine comprises:

a compound represented by the following formula (2) in an amount ranging from 1 μM to 100 mM:

(2)

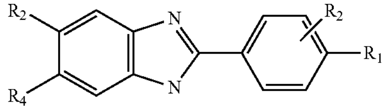

where $R_1$ represents a group selected from a hydroxy group represented by —OH; a haloalkoxy group represented by $—O—R_{1b}—X_{n1}$, wherein Rib is an alkyl group having 1 to 3 carbon atoms, X is a halogen selected from fluorine, chlorine, bromine, and iodine, and n1 is 1 to 3; a dialkylamino group represented by $—N(R_{1c})$ $(R_{1a})$, wherein Ric and Ria are each independently an alkyl group having 1 to 10 carbon atoms and may be the same or different from each other; a heterocyclic amine having 2 to 6 carbon atoms represented by $—N—(CH_2)_{n2}—$, wherein n2 is 2 to 6; bromine represented by —Br; iodine represented by —I; or a straight-chain hydrocarbon group having 2 to 5 carbon atoms represented by $—(CH_2)_{n3}—CH_3$, wherein n3 is 1 to 4;

$R_2$ represents hydrogen or a haloalkoxy group represented by $—O—R_{2a}—X_{n4}$, wherein $R_{2a}$ is a hydrocarbon group having 1 to 3 carbon atoms, X is a halogen selected from fluorine, chlorine, bromine, and iodine, and n4 is 1 to 3; and $R_3$ and $R_4$ represent a hydrogen atom, an alkyl group having 1 to 4 carbon atoms, or a halogen atom selected from fluorine, chlorine, bromine, and iodine, and $R_3$ and $R_4$ may be the same as or different from each other, and an additive, wherein the additive is a solvent, an excipient, a binding agent, a disintegrant, a lubricating agent, a stabilizer, or a suspending agent;

wherein the compound represented by formula (2) binds to a membrane-embedded rotor ring (c ring) of the V-ATPase of the bacterium to inhibit a $Na^+$-translocating activity of the V-ATPase, wherein the bacterium having V-ATPase is *Chlamydia trachomatis, Mycobacterium abscessus, Enterococcus faecium, Enterococcus durans, Enterococcus munditi, Enterococcus faecalis, Enterococcus malodoratus, Enterococcus cecorum, Enterococcus casseliflavus, Streptococcus agalactiae, Streptococcus sanguinis, Streptococcus constellatus, Streptococcus intermedius, Streptococcus gallolyticus, Streptococcus parasanguinis, Streptococcus anginosus, Streptococcus pyogenes, Streptococcus pneumoniae, Streptococcus pseudopneumoniae, Streptococcus mitis, Streptococcus canis, Streptococcus urinalis, Clostridium botulinum, Clostridium baratii, Clostridium argentinense, Clostridium chauvoei, Clostridium intestinale, Clostridium paraputrificum, Clostridium perfringens, Clostridium tetani, Clostridium difficile, Fusobacterium nucleatum, Fusobacterium necrophorum, Fusobacterium periodonticum, Abiotrophia* defective, *Aerococcus urinae, Aerococcus viridans, Facklamia hominis, Facklamia languida, Facklamia ignava, Facklamia sourekii, Alloiococcus otitis, Dolosigranulum pigrum, Granulicatella elegans*, or *Anaerotruncus colihominis.*

2. The method according to claim 1, wherein the compound represented by formula (2) is:

(V-161-01)

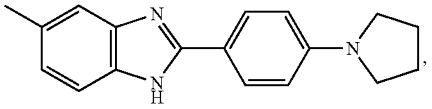

(V-161-02)

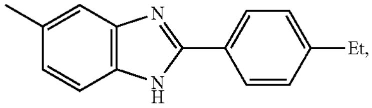

(V-161-03)

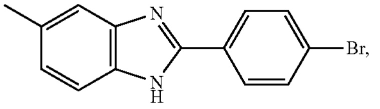

or (V-161-04)

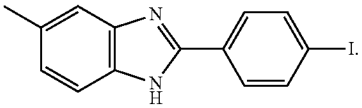

3. The method according to claim 1, wherein the compound represented by formula (2) is:

(V-161-01)

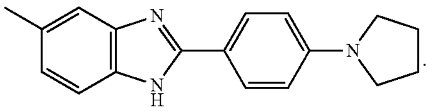

4. The method according to claim 1, wherein the compound represented by formula (2) is:

(V-161-02)

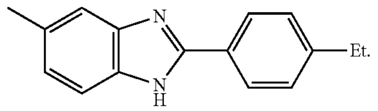

5. The method according to claim 1, wherein the compound represented by formula (2) is:

(V-161-03)

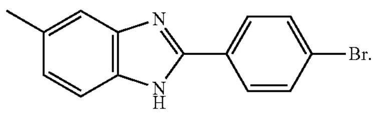

6. The method according to claim 1, wherein the compound represented by formula (2) is:

(V-161-04)

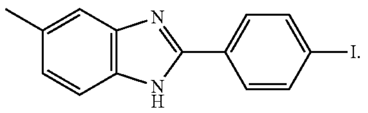

7. A method of suppressing growth of a bacterial flora containing a bacterium having V-ATPase and a bacterium having no V-ATPase in a subject, comprising the step of:

administering a medicine to the subject having the bacterial flora containing the bacterium having V-ATPase and the bacterium having no V-ATPase, wherein the medicine comprises:

a compound represented by the following formula (2) in an amount ranging from 1 μM to 100 mM:

(2)

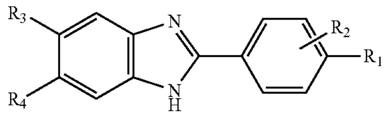

where $R_1$ represents a group selected from a hydroxy group represented by —OH; a haloalkoxy group represented by $—O—R_{1b}—X_{n1}$, wherein Rib is an alkyl group having 1 to 3 carbon atoms, X is a halogen selected from fluorine, chlorine, bromine, and iodine, and n1 is 1 to 3; a dialkylamino group represented by $—N(R_{1c})(R_{1a})$, wherein $R_{1c}$ and $R_{1d}$ are each independently an alkyl group having 1 to 10 carbon atoms and may be the same or different from each other; a heterocyclic amine having 2 to 6 carbon atoms represented by $—N—(CH_2)_{n2}—$, wherein n2 is 2 to 6; bromine represented by —Br; iodine represented by —I; or a straight-chain hydrocarbon group having 2 to 5 carbon atoms represented by $—(CH_2)_{n3}—CH_3$, wherein n3 is 1 to 4;

$R_2$ represents hydrogen or a haloalkoxy group represented by $—O—R_{2a}—X_{n4}$, wherein $R_{2a}$ is a hydrocarbon group having 1 to 3 carbon atoms, X is a halogen selected from fluorine, chlorine, bromine, and iodine, and n4 is 1 to 3; and $R_3$ and $R_4$ represent a hydrogen atom, an alkyl group having 1 to 4 carbon atoms, or a halogen atom selected from fluorine, chlorine, bromine, and iodine, and $R_3$ and $R_4$ may be the same as or different from each other, and an additive, wherein the additive is a solvent, an excipient, a binding agent, a disintegrant, a lubricating agent, a stabilizer, or a suspending agent;

wherein the compound represented by formula (2) binds to a membrane-embedded rotor ring (c ring) of the V-ATPase of the bacterium to inhibit a $Na^+$-translocating activity of the V-ATPase to selectively reduce the bacterium having V-ATPase from the bacterial flora containing the bacterium having V-ATPase and the bacterium having no V-ATPase, wherein the bacterium having V-ATPase is *Chlamydia trachomatis, Mycobacterium abscessus, Enterococcus faecium, Enterococcus durans, Enterococcus munditi, Enterococcus faecalis, Enterococcus malodoratus, Enterococcus cecorum, Enterococcus casseliflavus, Streptococcus agalactiae, Streptococcus sanguinis, Streptococcus constellatus, Streptococcus intermedius, Streptococcus gallolyticus, Streptococcus parasanguinis, Streptococcus anginosus, Streptococcus pyogenes, Streptococcus pneumoniae, Streptococcus pseudopneumoniae, Streptococcus mitis, Streptococcus canis, Streptococcus urinalis, Clostridium botulinum, Clostridium baratii, Clostridium argentinense, Clostridium chauvoei, Clostridium intestinale, Clostridium paraputrificum, Clostridium perfringens, Clostridium tetani, Clostridium difficile, Fusobacterium nucleatum, Fusobacterium necrophorum, Fusobacterium periodonticum, Abiotrophia* defective, *Aerococcus urinae, Aerococcus viridans, Facklamia hominis, Facklamia languida, Facklamia ignava, Facklamia sourekii, Alloiococcus otitis, Dolosigranulum pigrum, Granulicatella elegans*, or *Anaerotruncus colihominis.*

8. The method according to claim 7, wherein the compound represented by formula (2) is:

(V-161-01)

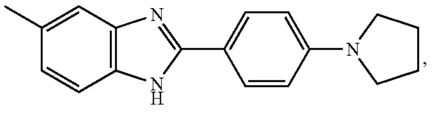

(V-161-02)

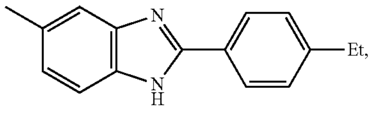

(V-161-03)

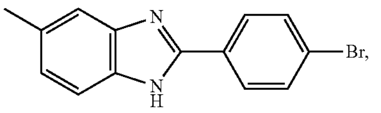

or (V-161-04)

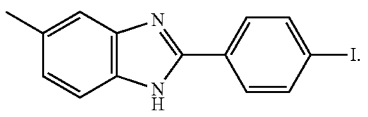

9. The method according to claim 7, wherein the compound represented by formula (2) is:
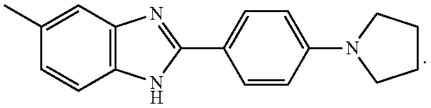
(V-161-01)
10. The method according to claim 7, wherein the compound represented by formula (2) is:
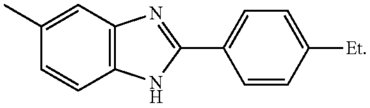
(V-161-02)
11. The method according to claim 7, wherein the compound represented by formula (2) is:
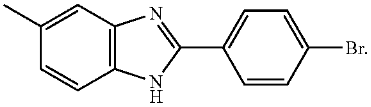
(V-161-03)
12. The method according to claim 7, wherein the compound represented by formula (2) is:
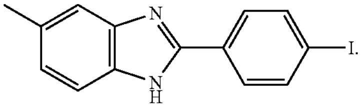
(V-161-04)
* * * * *